US012668164B2

(12) United States Patent
Orrington, II et al.

(10) Patent No.: US 12,668,164 B2
(45) Date of Patent: Jun. 30, 2026

(54) SYSTEM FOR MINIMIZING RISK OF TRANSMISSION OF INFECTION

(71) Applicant: James L. Orrington, II D.D.S., P.C., Chicago, IL (US)

(72) Inventors: James L. Orrington, II, Flossmoor, IL (US); Michael Prince, Chicago, IL (US); Hyunchul Kim, Chicago, IL (US)

( * ) Notice: Subject to any disclaimer, the term of this patent is extended or adjusted under 35 U.S.C. 154(b) by 904 days.

(21) Appl. No.: 16/943,133

(22) Filed: Jul. 30, 2020

(65) Prior Publication Data

US 2021/0354610 A1    Nov. 18, 2021
US 2023/0373369 A9    Nov. 23, 2023

Related U.S. Application Data

(63) Continuation of application No. 16/924,649, filed on Jul. 9, 2020.

(Continued)

(51) Int. Cl.
*B60N 2/75*      (2018.01)
*A61B 90/00*     (2016.01)
(Continued)

(52) U.S. Cl.
CPC .............. *B60N 2/793* (2018.02); *A61B 90/05* (2016.02); *A61F 9/045* (2013.01); *A61G 15/00* (2013.01);
(Continued)

(58) Field of Classification Search
CPC ......... A61B 90/05; A61F 9/045; A61G 15/00; A61G 15/10; A61G 15/14; B60N 2/793; B60N 2/767; B60N 2/797
See application file for complete search history.

(56) References Cited

U.S. PATENT DOCUMENTS 2,485,325 A    10/1949    Sloane
2,726,054 A    12/1955    Tompkins et al.
(Continued)

FOREIGN PATENT DOCUMENTS

CA        2140718 A      7/1996
CN      204788058 U     11/2015
(Continued)

OTHER PUBLICATIONS

Darrah, I., Bennett, J. S., Jones, B. W., & Hosni, M. H. (2019). Infectious Passenger Isolation System for Aircraft. ASHRAE Transactions, 125. (Year: 2019).*

(Continued)

*Primary Examiner* — Charles A Marmor, II
*Assistant Examiner* — Marc D. Honrath
(74) *Attorney, Agent, or Firm* — Chiacchio IP, LLC; Theodore J. Chiacchio

(57)                ABSTRACT

Disclosed herein are systems for minimizing the risk of transmission of SARS-CoV-2 and/or other infectious diseases between individuals in close proximity to one another. Said systems may comprise a substantially transparent shield component, a chamber component, and a suctioning component. The systems of the present disclosure are intended to remove any SARS-CoV-2 virus and/or other infectious agents that may be travelling within aerosols.

8 Claims, 27 Drawing Sheets

Related U.S. Application Data

(60) Provisional application No. 63/026,110, filed on May 17, 2020.

(51) Int. Cl.
| | |
|---|---|
| *A61F 9/04* | (2006.01) |
| *A61G 15/00* | (2006.01) |
| *A61G 15/10* | (2006.01) |
| *A61G 15/14* | (2006.01) |

(52) U.S. Cl.
CPC ............. *A61G 15/10* (2013.01); *A61G 15/14* (2013.01); *B60N 2/767* (2018.02); *B60N 2/797* (2018.02)

(56) References Cited

U.S. PATENT DOCUMENTS

| | | | |
|---|---|---|---|
| 3,377,082 A | | 4/1968 | Saunders |
| 3,877,691 A | * | 4/1975 | Foster ................ A61M 16/009 128/200.24 |
| 4,444,183 A | * | 4/1984 | Heckendorn ......... A61M 16/06 128/205.26 |
| 4,559,939 A | | 12/1985 | Levine et al. |
| 4,734,625 A | | 3/1988 | Geanous |
| 4,777,547 A | | 10/1988 | Eisner |
| 4,781,108 A | | 11/1988 | Nillson |
| 4,832,042 A | | 5/1989 | Poppendiek et al. |
| 4,936,318 A | * | 6/1990 | Schoolman .......... A61G 13/108 15/301 |
| 4,942,685 A | | 7/1990 | Lin |
| 4,949,714 A | | 8/1990 | Orr |
| 5,012,852 A | | 5/1991 | Blackhurst |
| 5,316,541 A | | 5/1994 | Fischer |
| D354,560 S | | 1/1995 | Chase |
| 5,497,295 A | | 3/1996 | Gehly |
| 5,620,407 A | | 4/1997 | Chang |
| 5,636,627 A | * | 6/1997 | Rochester ........... A61M 16/009 128/205.27 |
| 5,865,182 A | | 2/1999 | Chen |
| 6,309,222 B1 | | 10/2001 | Billingsley |
| 6,321,764 B1 | | 11/2001 | Gauger et al. |
| 6,322,754 B1 | | 11/2001 | Buchmann et al. |
| 6,338,675 B2 | | 1/2002 | Winkelman |
| 6,367,943 B1 | | 4/2002 | Tocci et al. |
| 6,471,579 B1 | | 10/2002 | Blackshear |
| 6,899,668 B2 | | 5/2005 | Paranjpe |
| 7,094,266 B2 | | 8/2006 | Montgomery |
| 7,207,694 B1 | | 4/2007 | Petrick |
| 7,503,890 B2 | | 3/2009 | Kubicsko et al. |
| 8,087,341 B2 | | 1/2012 | Adler |
| 8,234,822 B2 | | 8/2012 | Proctor et al. |
| 8,245,713 B2 | | 8/2012 | Paschal, Jr. et al. |
| 8,397,725 B2 | | 3/2013 | Slaker et al. |
| 8,568,501 B2 | | 10/2013 | Kelso |
| D704,934 S | | 5/2014 | Blinka et al. |
| D784,541 S | | 4/2017 | Hilbig et al. |
| 9,981,351 B2 | | 5/2018 | Vanier et al. |
| 10,016,251 B2 | | 7/2018 | Holman et al. |
| 10,016,252 B1 | | 7/2018 | Wren |
| 10,420,386 B1 | | 9/2019 | Jefferis et al. |
| 10,596,282 B2 | | 3/2020 | Gil et al. |
| 10,888,479 B1 | | 1/2021 | Gershon et al. |
| 10,925,561 B2 | | 2/2021 | Snow |
| D912,842 S | | 3/2021 | Chou et al. |
| D920,518 S | | 5/2021 | Takahashi |
| D926,462 S | | 8/2021 | Burgon et al. |
| D936,905 S | | 11/2021 | Jefferis et al. |
| 11,191,334 B2 | | 12/2021 | Aghazadeh et al. |
| D940,565 S | | 1/2022 | Nguyen et al. |
| D947,679 S | | 4/2022 | Hughes et al. |
| 11,317,986 B1 | * | 5/2022 | Ahearn ................. B01D 46/10 |
| 11,534,256 B2 | * | 12/2022 | Asamarai ............... A61B 90/57 |
| 2004/0129860 A1 | | 7/2004 | Thibaud |
| 2004/0177447 A1 | * | 9/2004 | Love .................... A61G 10/005 5/658 |
| 2004/0255937 A1 | | 12/2004 | Sun |
| 2005/0011035 A1 | | 1/2005 | Rukavina et al. |
| 2005/0085686 A1 | | 4/2005 | Yuen |
| 2005/0285547 A1 | | 12/2005 | Piepgras |
| 2006/0148397 A1 | | 7/2006 | Schultz et al. |
| 2006/0247487 A1 | * | 11/2006 | Arts .................... A61G 11/009 600/21 |
| 2007/0125224 A1 | | 6/2007 | Thomas |
| 2008/0033328 A1 | | 2/2008 | Chang |
| 2008/0212337 A1 | | 9/2008 | Mangiardi |
| 2008/0223384 A1 | | 9/2008 | Zabari |
| 2009/0088061 A1 | | 4/2009 | Le Beau |
| 2010/0279594 A1 | | 11/2010 | Peeler et al. |
| 2011/0202068 A1 | | 8/2011 | Diolaiti |
| 2011/0226123 A1 | | 9/2011 | Priebe et al. |
| 2011/0318702 A1 | | 12/2011 | Lockwood |
| 2012/0326627 A1 | | 12/2012 | McDaniel, Jr. |
| 2013/0101953 A1 | | 4/2013 | Stone et al. |
| 2014/0111977 A1 | | 4/2014 | Nyberg |
| 2014/0316455 A1 | | 10/2014 | Gnanashanmugam |
| 2014/0349561 A1 | | 11/2014 | Reiss et al. |
| 2015/0025300 A1 | * | 1/2015 | Hill ........................... A61L 9/22 600/21 |
| 2016/0074268 A1 | | 3/2016 | Breegi et al. |
| 2016/0249810 A1 | | 9/2016 | Darty et al. |
| 2016/0353055 A1 | | 12/2016 | Popescu et al. |
| 2017/0208878 A1 | * | 7/2017 | Kakinuma .............. A61F 9/045 |
| 2018/0023799 A1 | | 1/2018 | Lumaye et al. |
| 2018/0163978 A1 | | 6/2018 | Ziegler et al. |
| 2018/0236614 A1 | | 8/2018 | Holmes |
| 2019/0105740 A1 | | 4/2019 | Vanier |
| 2019/0330874 A1 | | 10/2019 | Pescovitz |
| 2019/0388290 A1 | | 12/2019 | Comunale |
| 2020/0000541 A1 | | 1/2020 | Clemens |
| 2020/0005676 A1 | * | 1/2020 | Kubota .................... G09B 9/00 |
| 2020/0016774 A1 | * | 1/2020 | Keen ...................... F16D 13/648 |
| 2021/0290793 A1 | * | 9/2021 | Tung .................. A41D 13/1184 |
| 2021/0330419 A1 | * | 10/2021 | Danner ................ A61G 10/005 |
| 2021/0346564 A1 | | 11/2021 | Jetter |
| 2021/0353380 A1 | | 11/2021 | Sellars et al. |
| 2021/0353469 A1 | | 11/2021 | Orrington, II |
| 2022/0084199 A1 | | 3/2022 | Lee et al. |
| 2022/0142269 A1 | | 5/2022 | Orrington, II et al. |

FOREIGN PATENT DOCUMENTS

| | | | | |
|---|---|---|---|---|
| CN | 106581867 | | 4/2017 | |
| CN | 210472180 | | 5/2020 | |
| EP | 0463282 | A1 | 1/1992 | |
| EP | 1672338 | | 6/2006 | |
| EP | 3895653 | A1 * | 10/2021 | ............. A61B 46/10 |
| EP | 4093317 | A4 | 2/2024 | |
| EP | 4142643 | A4 | 7/2024 | |
| IN | 427 | | 4/2010 | |
| IN | 427/DEL/2010 | | 4/2010 | |
| JP | 49688 | A | 3/1993 | |
| JP | H0549688 | A | 3/1993 | |
| JP | H06038933 | | 5/1994 | |
| JP | H08033659 | | 2/1996 | |
| JP | 2002303436 | A | 10/2002 | |
| JP | 2007130333 | | 5/2007 | |
| JP | 2015037475 | A | 2/2015 | |
| JP | 2016-86839 | A | 5/2016 | |
| JP | 2016086839 | A | 5/2016 | |
| JP | 2011-25028 | | 12/2016 | |
| JP | 6368005 | | 8/2018 | |
| JP | 1683418 | S | 4/2021 | |
| KR | 20150033913 | A * | 4/2014 | |
| RU | 80336 | U1 * | 2/2009 | |
| RU | 2008138178 | U | 2/2009 | |
| WO | WO2000045768 | A1 | 8/2000 | |

(56)                    References Cited

FOREIGN PATENT DOCUMENTS

| WO | WO 2021236241 A1 | 11/2021 |
| WO | WO 2021236245 A1 | 11/2021 |

OTHER PUBLICATIONS

International Search Report for PCT Application No. PCT/US21/025724, dated Jul. 15, 2021; and associated written opinion.

Aura Raskin, Architects, Engineers, and Physicians Develop COVID-19 Patient Isolation Hood, Architectural Record, Apr. 14, 2020, pp. 3-4, ePublishing, Chicago, Illinois, U.S.

Teju Hari Krishna, Researchers design ventilation hoods for hospital beds to help contain COVID-19 spread, Apr. 9, 2020, pp. 1-2, The University of Melbourne, Melbourne, Australia.

Image No. 1, available at https://unicoredental.com/.

Image No. 2, available at https://www.ergonomic-products.com/safe-t-shield/.

Image No. 3, available at https://www.ergonomic-products.com/safe-t-shield/.

Image No. 4, available at https://www.ergonomic-products.com/safe-t-shield/.

Image No. 5, available at https://unicoredental.com/.

Google Search Results.

Dentistry biggest problem has been solved! Airguard™, Airguard, Youtube, [Post date: Feb. 24, 2021], [Site seen May 26, 2022], Seen at URL: https://www.youtube.com/watch?v=ARYY-09G.

Dental Face Shield, Classical Designs, [Post Date unknown], [Site seen May 26, 2022], Seen at URL: https://glassicaldesigns.com/product/dental-face-shield/ (Year: 2022).

By Anahad O'connor; Really? Flu Is Spread Primarily Through Close Contact; published Feb. 11, 2013; The New York Times (Year: 2013).

Airguard LT. Airguard, [Post date: Feb. 15, 2021], [Site seen May 26, 2022], Seen at URL: https://mobile.twitter.com/AirGuardHealth/status/1361314680480927750?cxt=HHwWjMC42aif.

* cited by examiner

SYSTEM FOR MINIMIZING RISK OF TRANSMISSION OF INFECTION

CROSS-REFERENCE TO RELATED APPLICATIONS

The present application claims priority to U.S. Provisional Patent Application No. 63/026,110 filed on May 17, 2020 and is a continuation of U.S. patent application Ser. No. 16/924,649, filed on Jul. 9, 2020. The contents of said applications are incorporated herein by reference.

FIELD OF THE INVENTION

The present disclosure relates to systems designed to minimize the risk of transmission of the COVID-19 virus and/or other sources of infection in environments where there is a high risk of transmission due to individuals being in close physical proximity to one another. More particularly, the disclosure relates to systems comprising aerosol shielding and suctioning features installable to an object such as a chair over which the shield component has been placed.

BACKGROUND

COVID-19 is an infectious disease caused by severe acute respiratory syndrome coronavirus 2 (SARS-CoV-2). The first cases of COVID-19 were reported in December, 2019, in Wuhan, China. Since that time, the virus has spread throughout the world, resulting in a global pandemic. More than 15.4 million patients have been diagnosed with COVID-19 across more than 213 countries and territories. As of the date of this disclosure, there have been more than 631,000 reported deaths due to COVID-19.

COVID-19 may be transmitted via droplet contact (e.g., coughing and sneezing); direct physical contact; indirect physical contact (e.g., touching a contaminated surface); and airborne transmission. The primary way through which COVID-19 is transmitted, however, is through small droplets produced by coughing, sneezing, and talking, where individuals are in close physical proximity to one another. COVID-19 may be transmitted by persons infected with the virus who have not exhibited any symptoms. Future effects of COVID-19 remain in question, as no known solution exists to mitigate or eliminate these undesirable conditions conducive to ongoing transmission.

Close physical proximity between people increases the risk of transmitting COVID-19 because COVID-19 may be transmitted via at least droplet contact (e.g., coughing and sneezing); direct physical contact; indirect physical contact (e.g., touching a contaminated surface); and airborne transmission. Social distancing, also referred to as physical distancing, is one of the primary tactics that have been utilized throughout the world to attempt to contain the spread of the COVID-19 virus. Social distancing comprises maintaining certain minimum physical distances between individuals and reducing the number of times that individuals come into close physical contact with one another. However, not all activities permit of maintaining sufficient minimum physical distances. For example, many healthcare workers must come within close proximity to their patients in order to perform their duties. Where close physical proximity between people cannot be avoided, there exists a need for a system that is effective in reducing the risk of transmitting COVID-19.

Particles are classified based on size. Coarse particles are 2.5 to 10 microns. Fine particles are less than 2.5 microns. Ultrafine particles are those less than 0.1 microns in size. A human nose generally filters particles larger than 10 microns. If a particle is less than 10 microns, it can enter the respiratory system. If a particle is less than 2.5 microns, it can enter the alveoli. An ultrafine particle can enter the bloodstream and target organs. COVID-19 exists as ultrafine particles.

Current research suggests that most respiratory transmission of COVID-19 occurs through large respiratory droplets. Such large droplets typically fall to the ground after travelling approximately six feet at the most. Activity such as coughing and sneezing, however, can aerosolize the droplets so that they can travel further thereby increasing the risk of transmission (i.e., where the droplets are carrying COVID-19). When aerosolized, COVID-19 can travel up to approximately 20 feet and will remain suspended in the air longer than when not aerosolized. In addition to coughing and sneezing, respiratory droplets are routinely aerosolized in the practice of dentistry.

Dentists who utilize aerosolization in their practice, and therefore their staff as well, are at a high risk of becoming infected with COVID-19. Such dentists' patients are likewise at high risk of becoming infected from the dentist, as well as their dental assistants in the immediate area when being treated. Most such risk results from splatter and droplet transmission to the mid-face of the dentist and assistant and to the nasal area of the patient.

SUMMARY

Systems enabled by this disclosure advantageously solve deficiencies known in the current state of the art. In one embodiment enabled by this disclosure, a system is enabled that advantageously enhances effectiveness in reducing the risk of transmitting COVID-19 by mitigating direct, indirect, and/or other contact between individuals. In one embodiment enabled by this disclosure, a system for minimizing risk of transmission may comprise a shield component, a chamber component, a suctioning component for suctioning aerosol attached to the interior surface of said shield component out of the space between said shield component and an individual occupying an object such as a chair over which the shield component has been placed.

According to an embodiment contemplated by this disclosure, a substantially transparent shield component is operatively attached to a dolly and is extendable from said dolly over an individual such as, without limitation, a patient occupying a dental chair, a patient occupying a hospital bed, an individual occupying a seat in an automobile, or an individual occupying a seat in an aircraft. According to another embodiment contemplated by this disclosure, the substantially transparent shield component may be operatively attached to a ceiling and extend downward from the ceiling over an individual such as, without limitation, a patient occupying a dental chair. According to an aspect of the present disclosure, the chamber component may further comprise diodes emitting ultraviolet light. According to another aspect of the present disclosure, such as, without limitation, where the substantially transparent shield component is operatively attached to a dental chair, the substantially transparent shield component may further comprise magnifying material and/or supplemental lighting to enhance visibility, such as, without limitation, within the mouth of a patient occupying the dental chair. According to an aspect of this disclosure, the suctioning component may comprise a device capable of creating a vacuum and may comprise an air filter.

According to an embodiment of the present disclosure, the system may comprise a single integrated unit comprising a substantially transparent shield component, a chamber component, and a suctioning component as disclosed herein.

According to another embodiment of the present disclosure, the system may further comprise a docking station that may serve as a source of power for the components of the system.

DETAILED DESCRIPTION

Figure 1A:
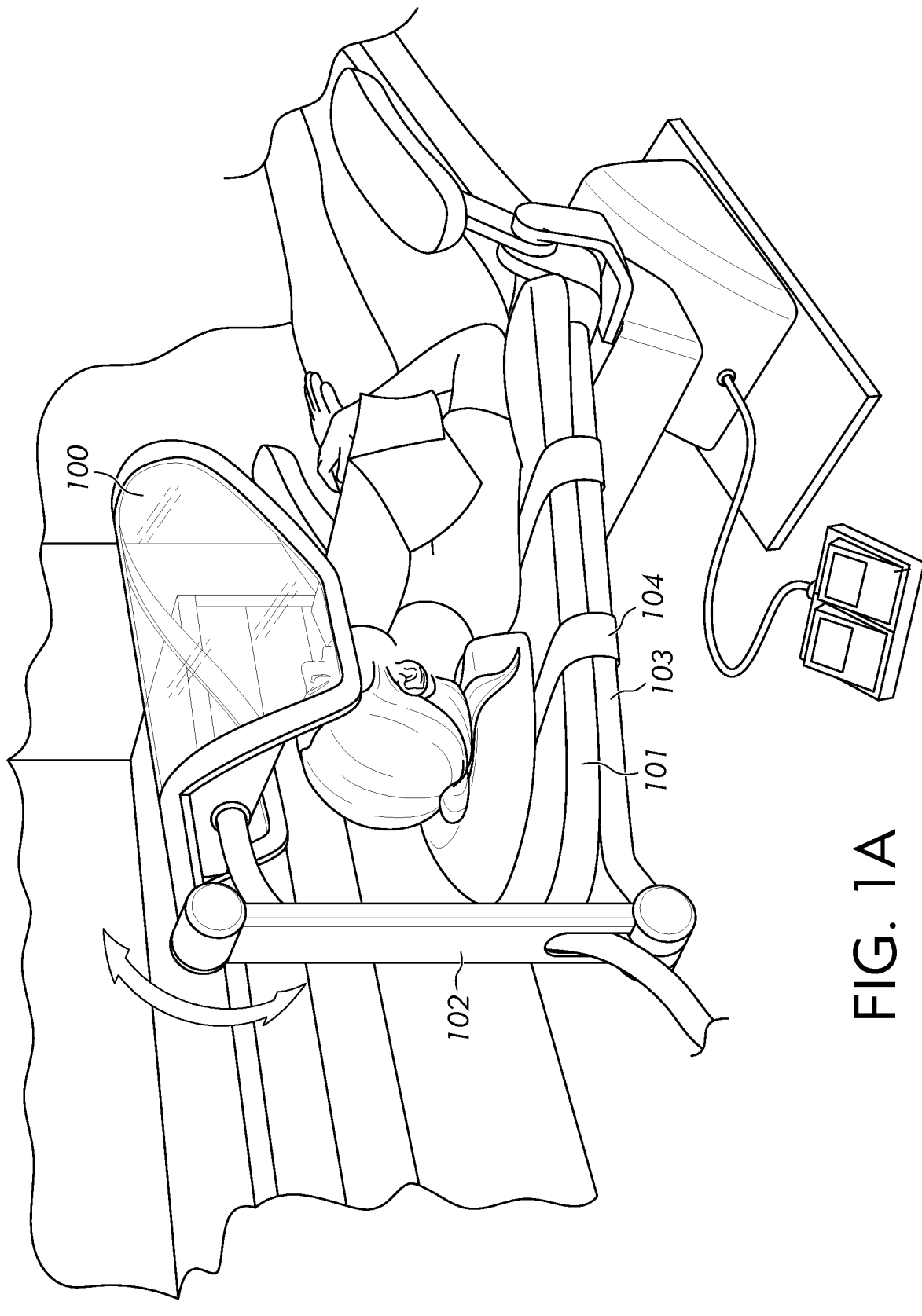
FIG. 1A is a perspective view of a system of the present disclosure wherein a patient is occupying a dental chair as contemplated by the present disclosure and wherein the substantially transparent shield component is attached to the chair by hook-and-loop fasteners.

The following disclosure is provided to describe various embodiments of a system intended to minimize the risk of transmission of COVID-19 and other viruses and infectious agents that may be transmitted between individuals in close physical proximity and/or who may interact with common surfaces or objects. Skilled artisans will appreciate additional embodiments and uses of the systems that extend beyond the examples of this disclosure. Terms included by any claim are to be interpreted as defined within this disclosure. Singular forms should be read to contemplate and disclose plural alternatives. Similarly, plural forms should be read to contemplate and disclose singular alternatives. Conjunctions should be read as inclusive except where stated otherwise.

Expressions such as "at least one of A, B, and C" should be read to permit any of A, B, or C singularly or in combination with the remaining elements. Additionally, such groups may include multiple instances of one or more elements in that group, which may be included with other elements of the group. All numbers, measurements, and values are given as approximations unless expressly stated otherwise.

Terms and expressions used throughout this disclosure are to be interpreted broadly. Terms are intended to be understood respective to the definitions provided by this specification. Technical dictionaries and common meanings understood within the applicable art are intended to supplement these definitions. In instances where no suitable definition can be determined from the specification or technical dictionaries, such terms should be understood according to their plain and common meaning. However, any definitions provided by the specification will govern above all other sources.

Various objects, features, aspects, and advantages described by this disclosure will become more apparent from the following detailed description, along with the accompanying drawings.

For the purpose of clearly describing the components and features discussed throughout this disclosure, some frequently used terms will now be defined, without limitation. The term "COVID-19," as it is used throughout this disclosure, is defined as an infectious disease caused by severe acute respiratory syndrome coronavirus 2 (SARS-CoV-2). The term "aerosol," as it is used throughout this disclosure, is defined as a suspension of fine solid particles or liquid droplets in air or another gas. The term "universal mount," as it is used throughout this disclosure, is defined as a universal clamp together with one or more compatible mounts. The term "individual," as it is used throughout this disclosure, should not be interpreted in any limiting manner, should be interpreted broadly, and should be interpreted, without limitation, as synonymous with "subject."

Various aspects of the disclosure will now be described in detail, without limitation. In the following disclosure, systems for minimizing risk, such as due to individuals' close physical proximity to one another, of transmission of COVID-19 will be discussed. Those of skill in the art will appreciate that alternative labeling of the systems may be provided, which is consistent with the scope and spirit of this disclosure. Skilled readers should not view the inclusion of any alternative labels as limiting in any way.

Figure 1B:
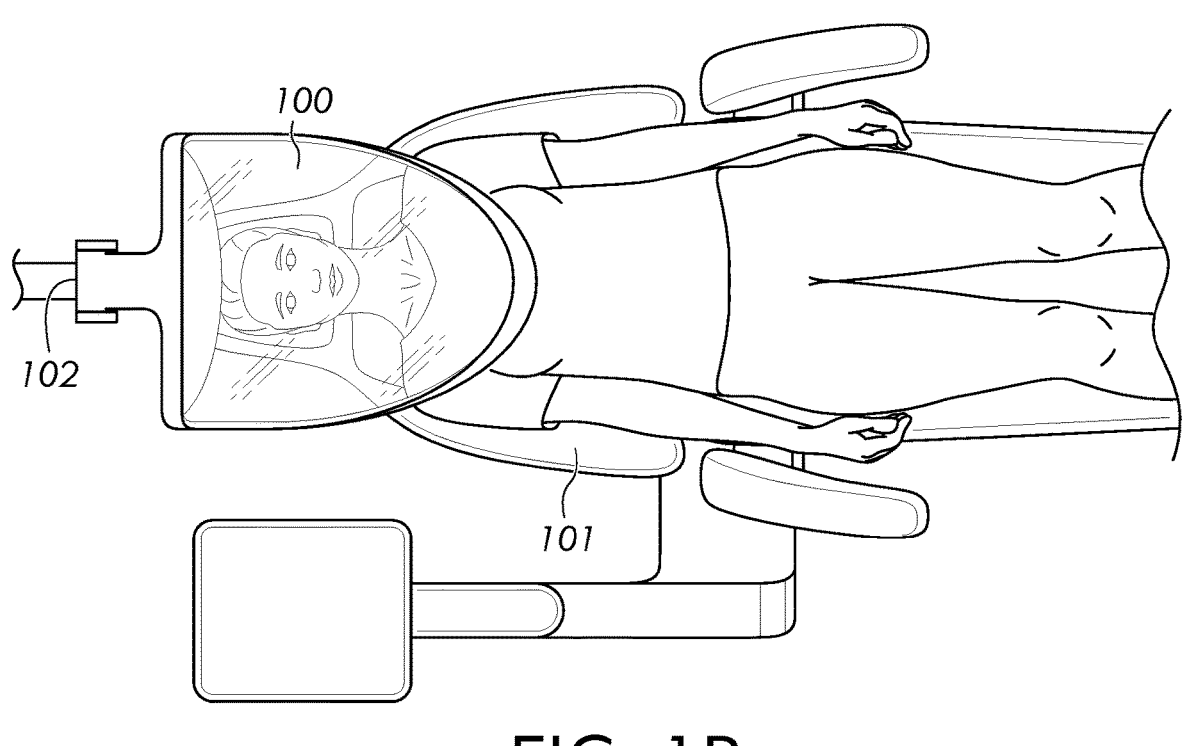
FIG. 1B is a top plan view of a system of the present disclosure wherein a patient is occupying a dental chair as contemplated by the present disclosure and wherein the substantially transparent shield component is attached to the chair by hook-and-loop fasteners.
Figure 1C:
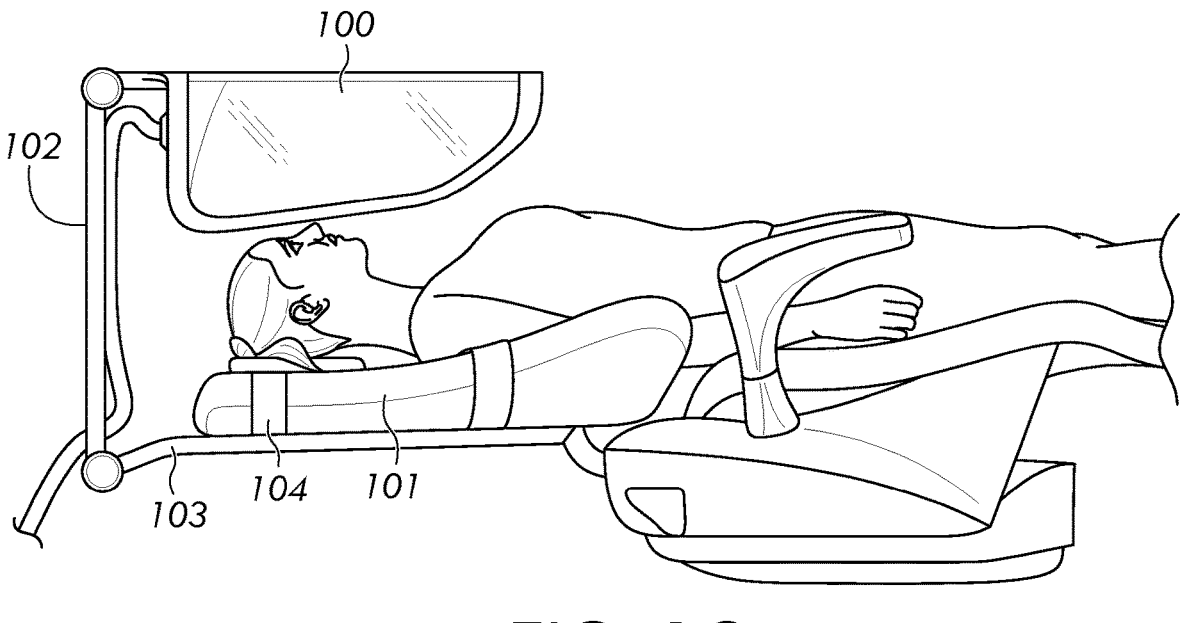
FIG. 1C is a side elevation view of a system of the present disclosure wherein a patient is occupying a dental chair as contemplated by the present disclosure and wherein the substantially transparent shield component is attached to the chair by hook-and-loop fasteners.
Figure 2A:
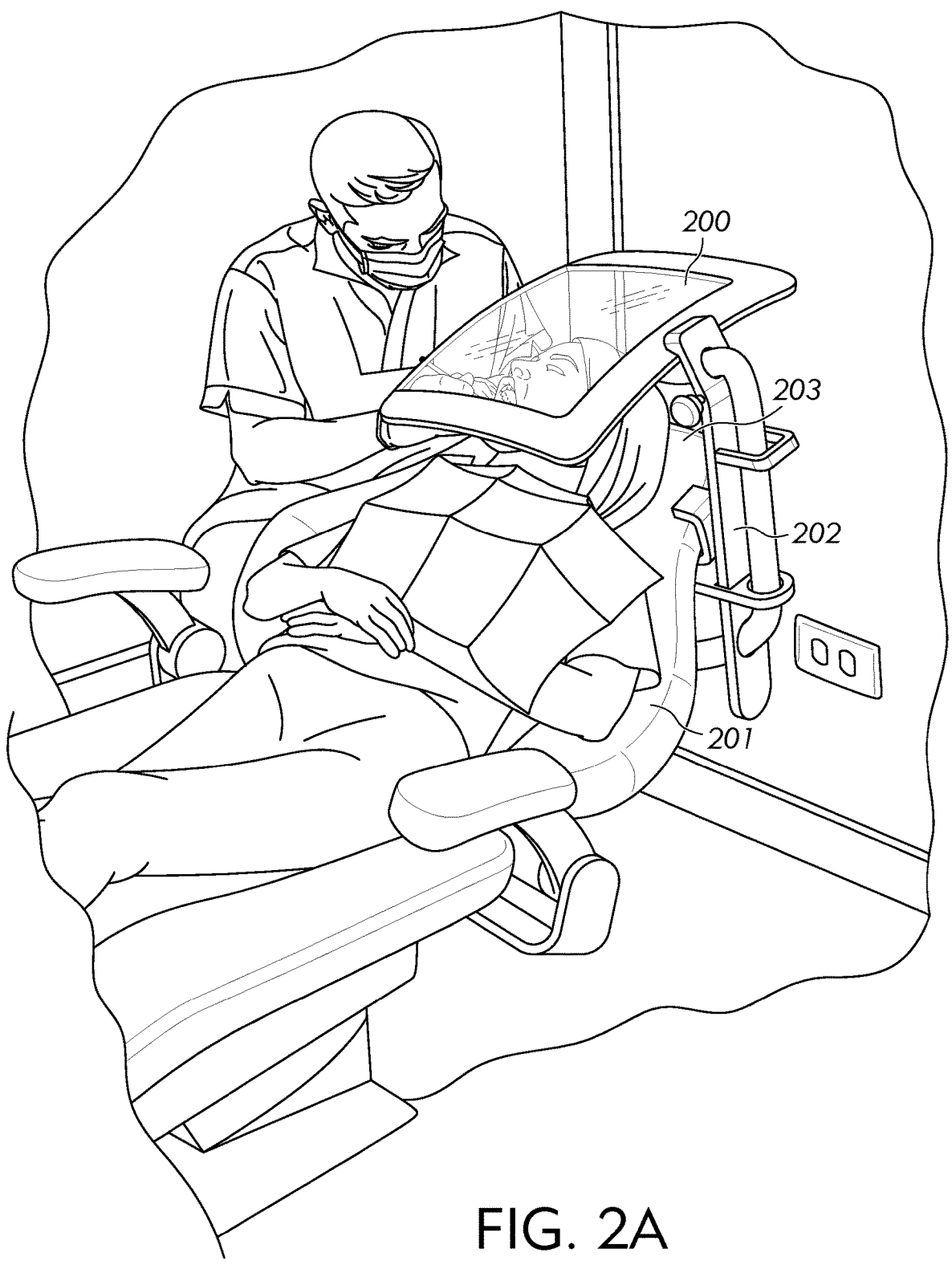
FIG. 2A is a perspective view of a system of the present disclosure wherein a patient is occupying a dental chair as contemplated by the present disclosure and wherein the substantially transparent shield component is attached to the dental chair by a rotatable arm attached to the head rest of the dental chair.
Figure 2B:
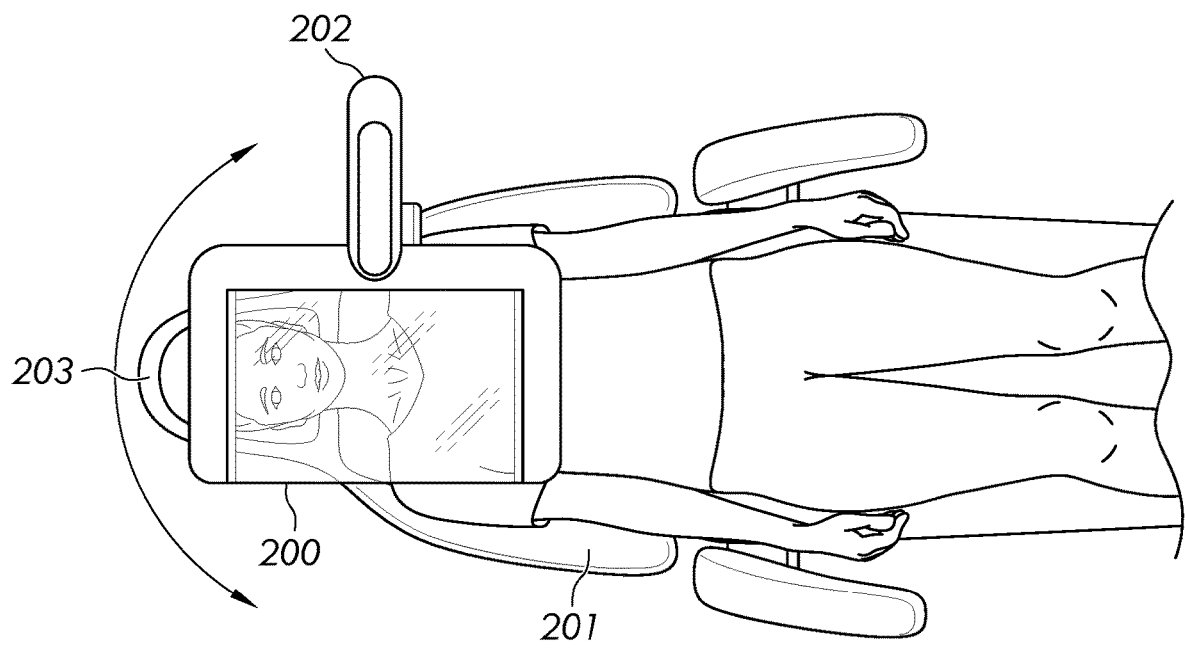
FIG. 2B is a top plan view of a system of the present disclosure wherein a patient is occupying a dental chair as contemplated by the present disclosure and wherein the substantially transparent shield component is attached to the dental chair by a rotatable arm attached to the head rest of the dental chair.
Figure 2C:
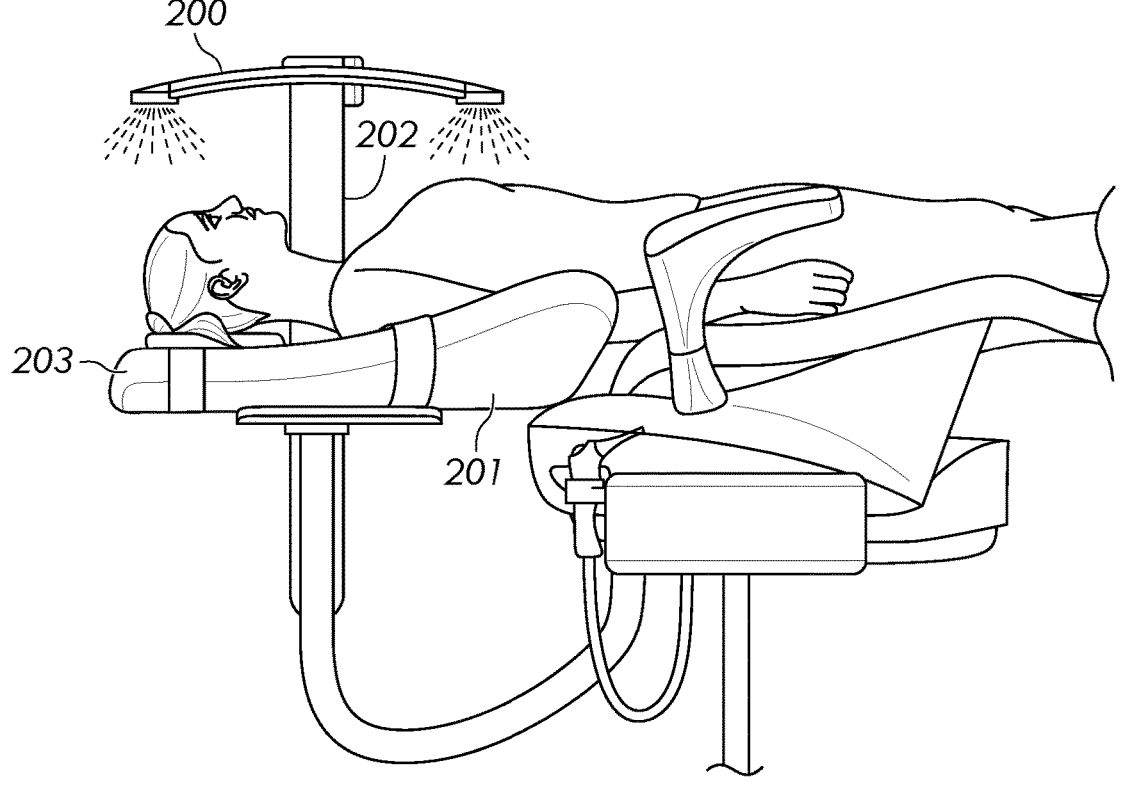
FIG. 2C is a side elevation view of a system of the present disclosure wherein a patient is occupying a dental chair as contemplated by the present disclosure and wherein the substantially transparent shield component is attached to the dental chair by a rotatable arm attached to the head rest of the dental chair.

Referring now to FIGS. 1-13, systems enabled by this disclosure will be discussed in greater detail. The substantially transparent shield component contemplated by the present disclosure 100, 200, 300, 400, 500, 600, 700 800, 900, 1000, 1100, 1200, 1300, 1400 may be operatively attached to any number of objects including, without limitation, a chair (such as, without limitation, a chair in a dentist's office 101, 201, 301, 401, 501, 701, 801, 901, 1001, 1101, 1201, 1301), a hospital bed, a seat in an automobile, a seat in an aircraft 1401, a freestanding base 902, which may be adjustable in height and rotatable 360 degrees around a horizontal axis, a transportable dolly 804, or a ceiling 702. The substantially transparent shield component may be attached to said objects by any suitable connecting means, which means would be readily appreciated by those skilled in the art. By way of example only, as depicted in FIG. 1, the substantially transparent shield component may be connected to the back of a chair by hook-and-loop fasteners 104. FIGS. 1-13 depict embodiments contemplated by the present disclosure where the substantially transparent shield component extends over a patient occupying a chair 101, 201, 301, 401, 501, 701, 801, 901, 1001, 1101, 1201, 1301, for example, in a dentist's office.

Without limitation, the substantially transparent shield component of the present disclosure may be operatively attached to objects of the nature contemplated by this disclosure by an arm 102, 202, 302, 402, 502, 601, 703, 802, 1002, 1103, 1203, 1302. The arm may be rotatable, including, without limitation, rotatable around the head of a patient occupying a dentist's chair to which the substantially transparent shield component, through said arm, may be attached. The arm may be collapsible and extendable. The substantially transparent shield component may be attached to the chair or other object via other suitable means as will be readily appreciated by those skilled in the art.

The arm may be attached to the dentist's chair or other object by any suitable means, which means would be readily appreciated by the skilled artisan. Without limitation, said attachment may be by means of a universal mount 405.

The substantially transparent shield component of the present disclosure may be curved. The substantially trans-parent shield component of the present disclosure may comprise protrusions to accommodate the curvature of an individual's face.

The substantially transparent shield component of the present disclosure may be removable. The substantially transparent shield component of the present disclosure may be disposable.

Where the substantially transparent shield component of the present disclosure is attached to a chair such as, without limitation, a chair for patients in a dentist's office, the substantially transparent shield component may be so attached at any number of locations on the chair, including, without limitation, the back of the chair 103, the arm rest of the chair 303, or the head rest of the chair 203.

Figure 8A:
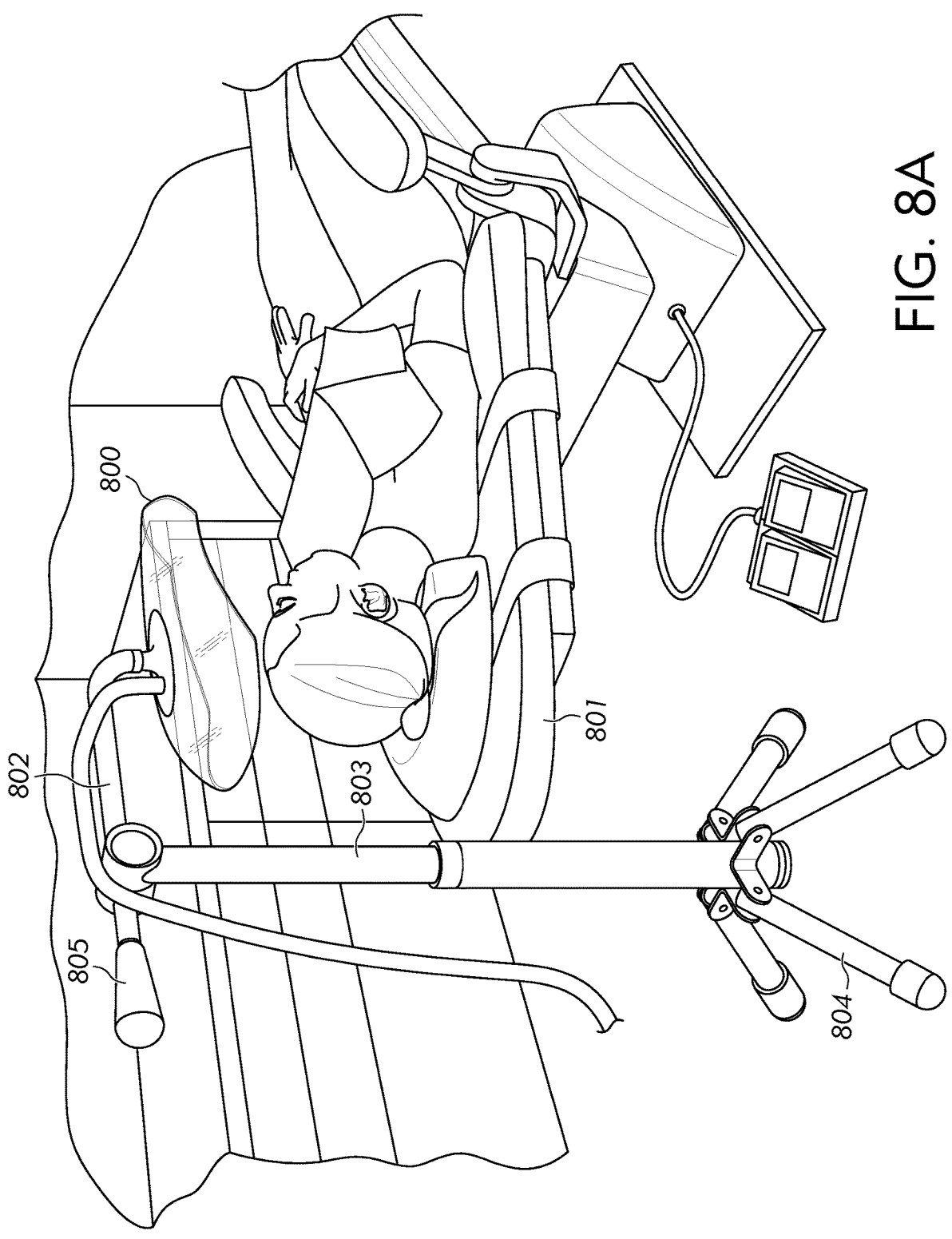
FIG. 8A is a perspective view of a system of the present disclosure wherein a patient is occupying a dental chair as contemplated by the present disclosure and wherein the substantially transparent shield component is connected to and extends from a rotatable freestanding base.
Figure 8B:
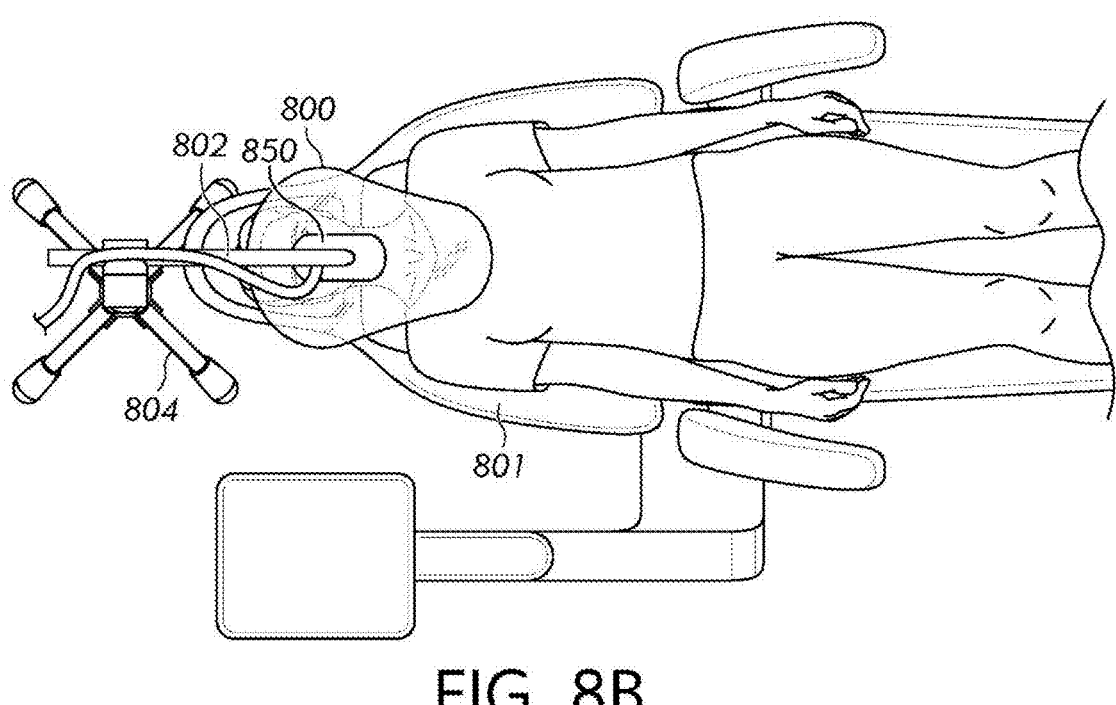
FIG. 8B is a top plan view of a system of the present disclosure wherein a patient is occupying a dental chair as contemplated by the present disclosure and wherein the substantially transparent shield component is connected to and extends from a rotatable freestanding base.
Figure 8C:
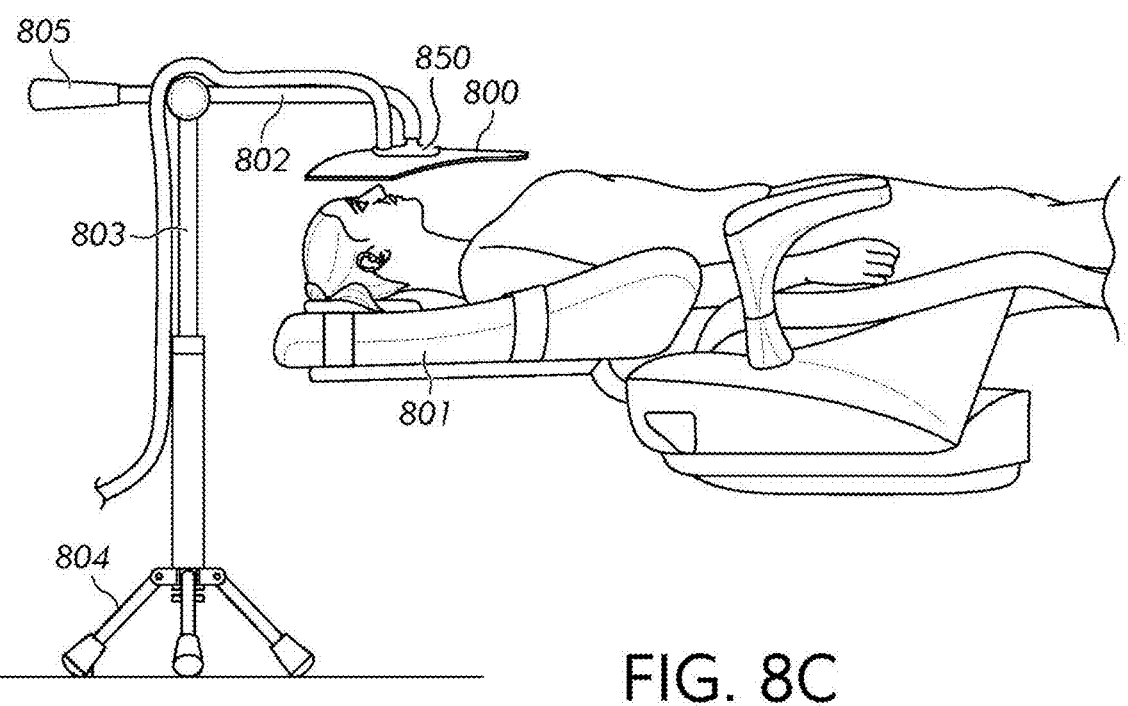
FIG. 8C is a side elevation view of a system of the present disclosure wherein a patient is occupying a dental chair as contemplated by the present disclosure and wherein the substantially transparent shield component is connected to and extends from a rotatable freestanding base.
Figure 9A:
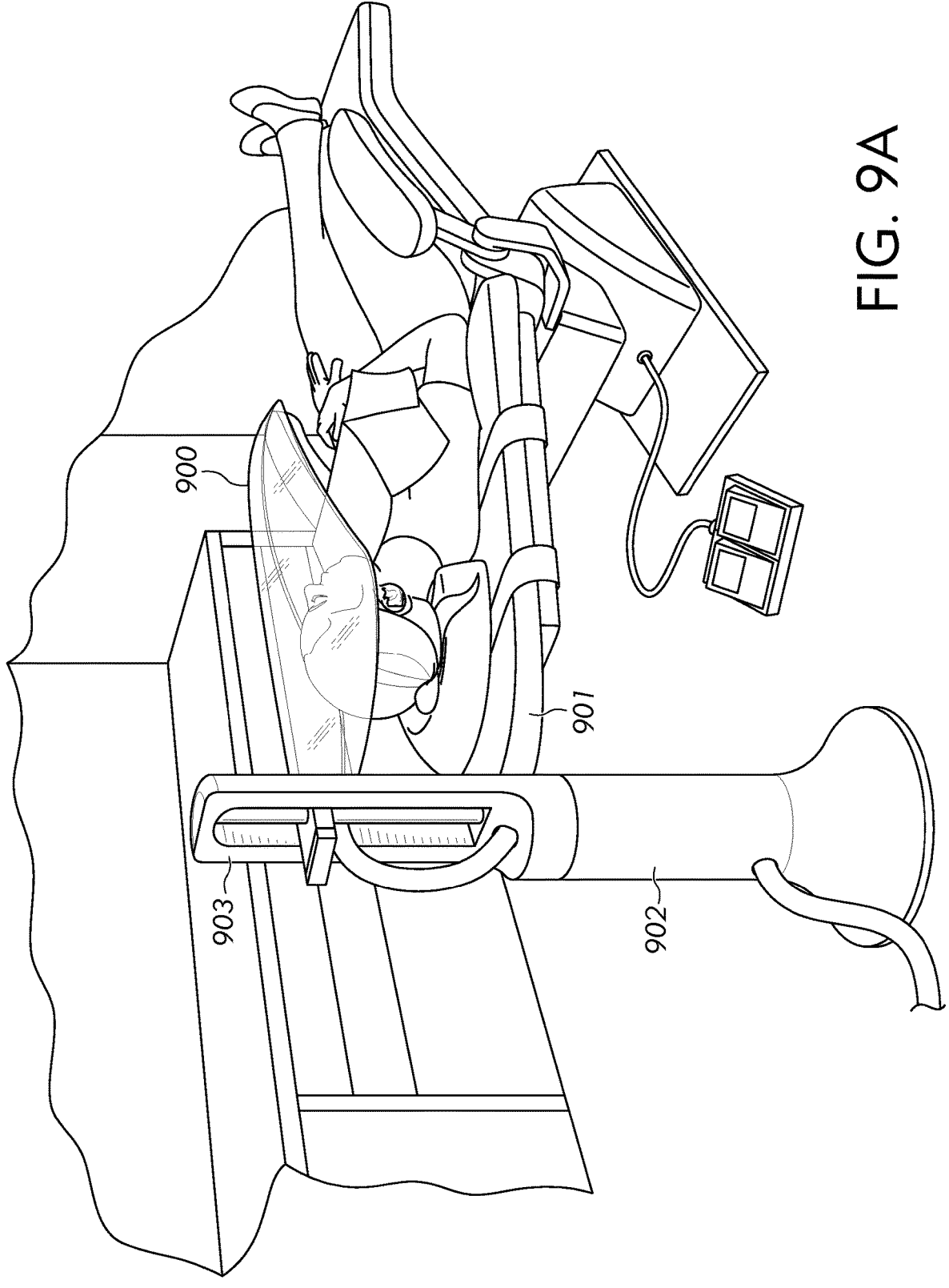
FIG. 9A is a perspective view of a system of the present disclosure wherein a patient is occupying a dental chair as contemplated by the present disclosure and wherein the substantially transparent shield component is connected to and extends from a rotatable freestanding base wherein the height of said base is adjustable using a handle.
Figure 9B:
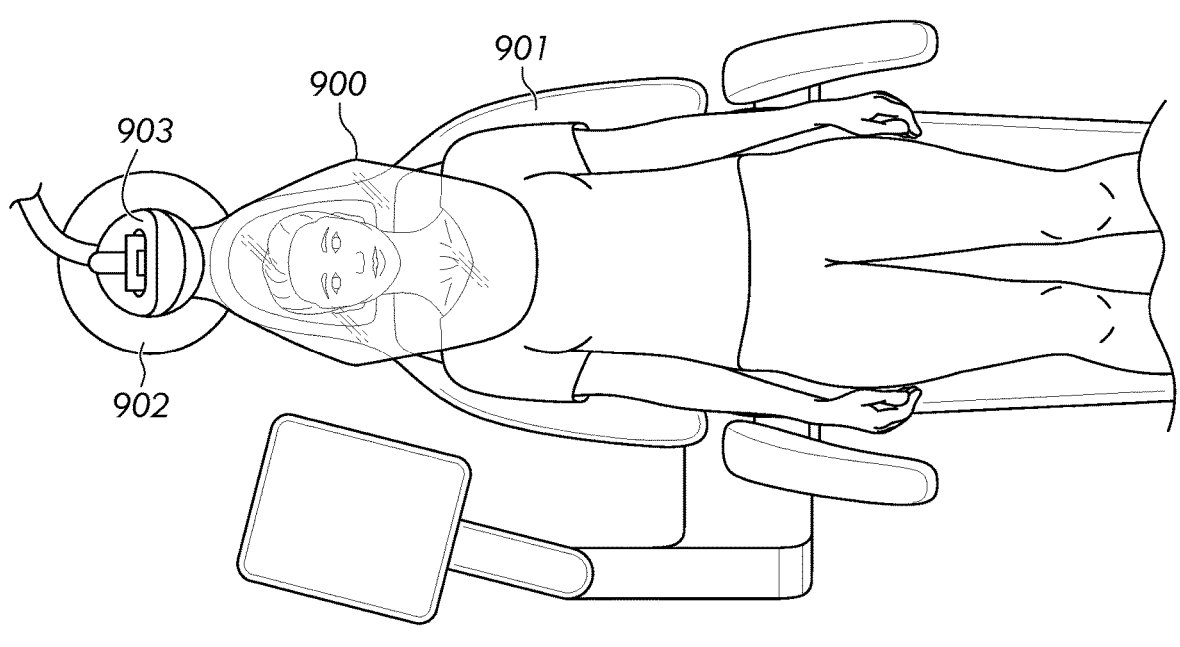
FIG. 9B is a top plan view of a system of the present disclosure wherein a patient is occupying a dental chair as contemplated by the present disclosure and wherein the substantially transparent shield component is connected to and extends from a rotatable freestanding base wherein the height of said base is adjustable using a handle.
Figure 9C:
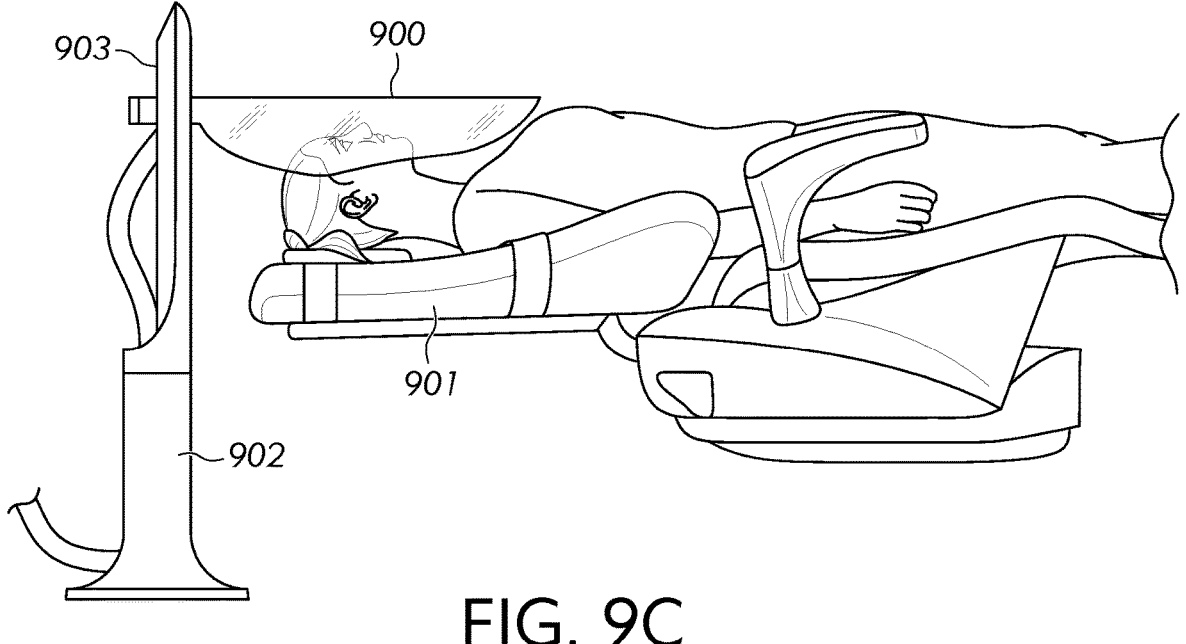
FIG. 9C is a side elevation view of a system of the present disclosure wherein a patient is occupying a dental chair as contemplated by the present disclosure and wherein the substantially transparent shield component is connected to and extends from a rotatable freestanding base wherein the height of said base is adjustable using a handle.
Figure 10A:
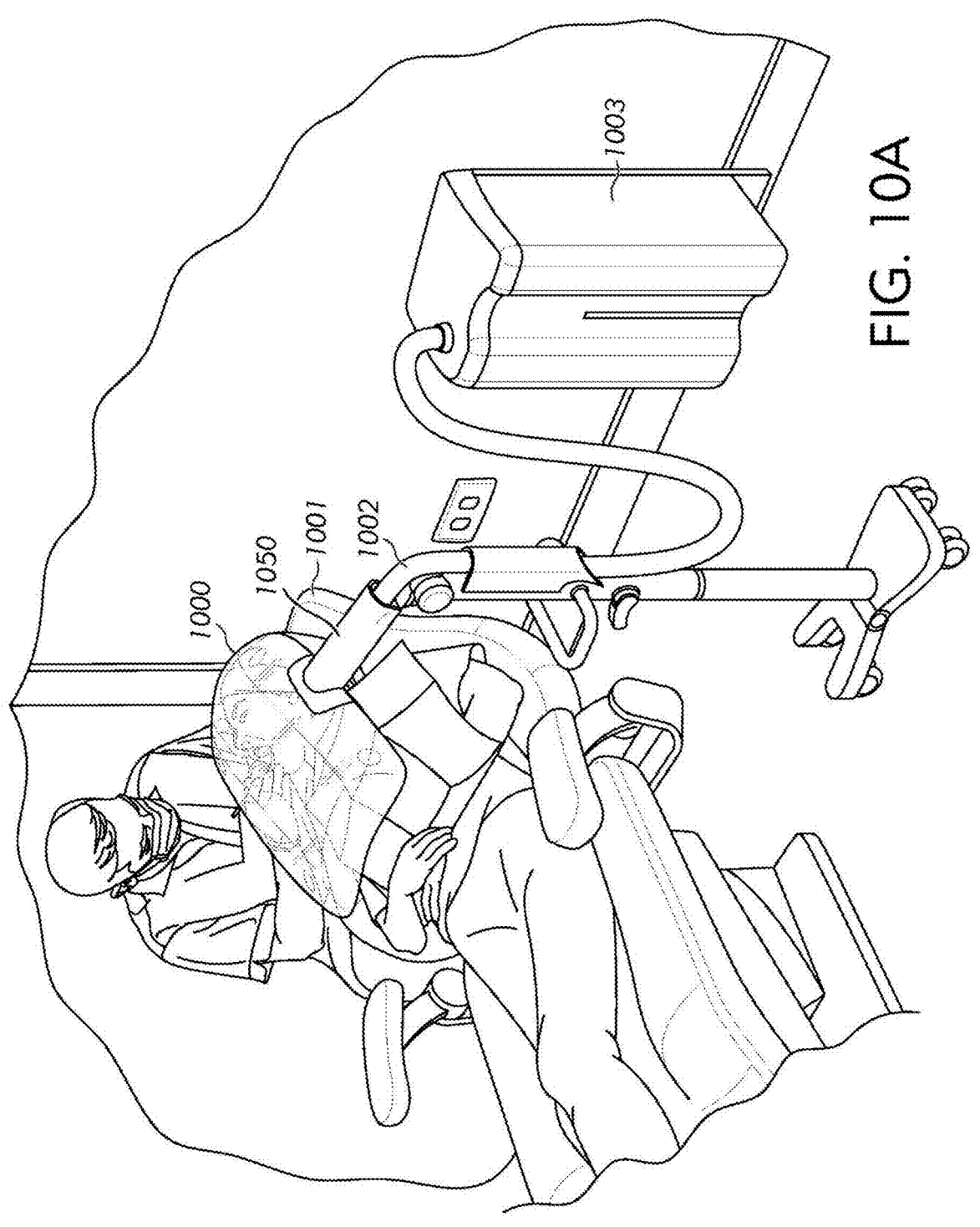
FIG. 10A is a perspective view of a system of the present disclosure wherein a patient is occupying a dental chair as contemplated by the present disclosure and wherein the suctioning component of the system is mounted to a wall adjacent to a dental chair occupied by a patient.
Figure 10B:
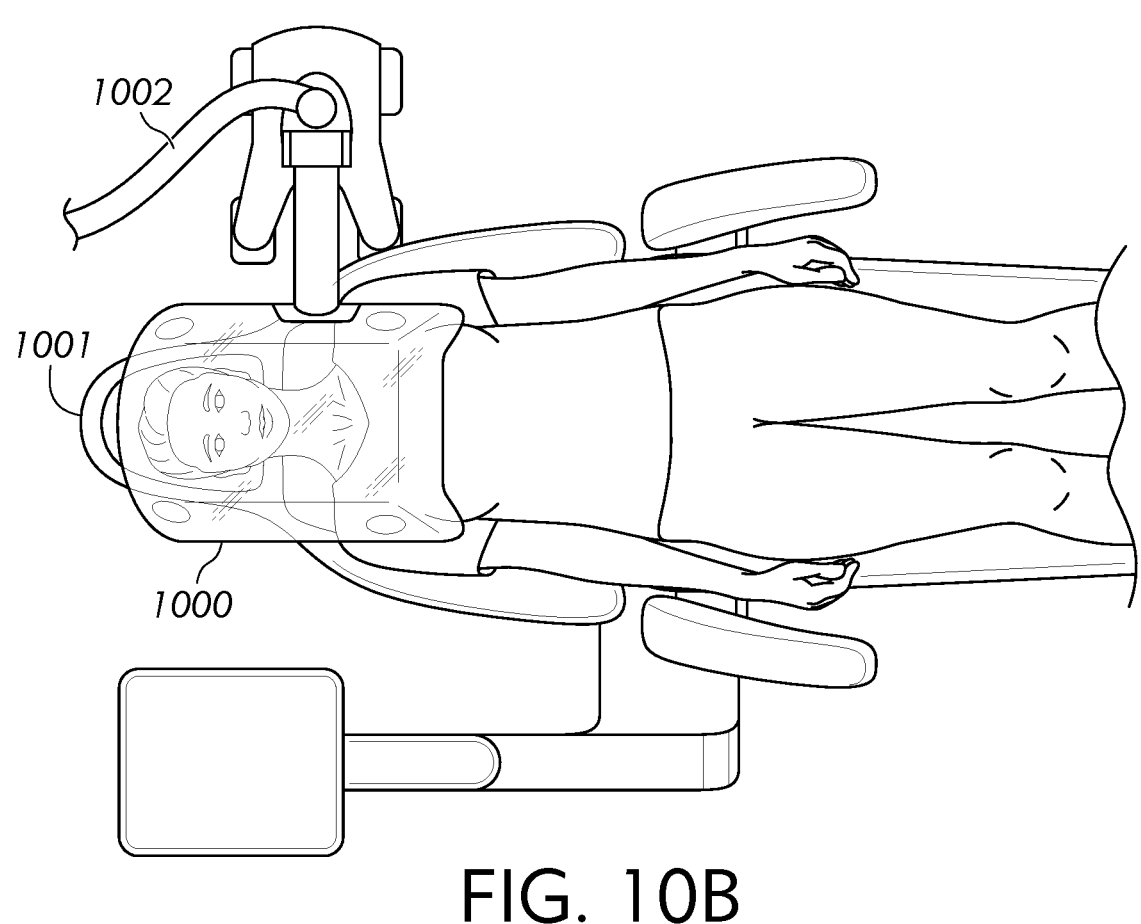
FIG. 10B is a top plan view of a system of the present disclosure wherein a patient is occupying a dental chair as contemplated by the present disclosure and wherein the suctioning component of the system is mounted to a wall adjacent to a dental chair occupied by a patient.
Figure 10C:
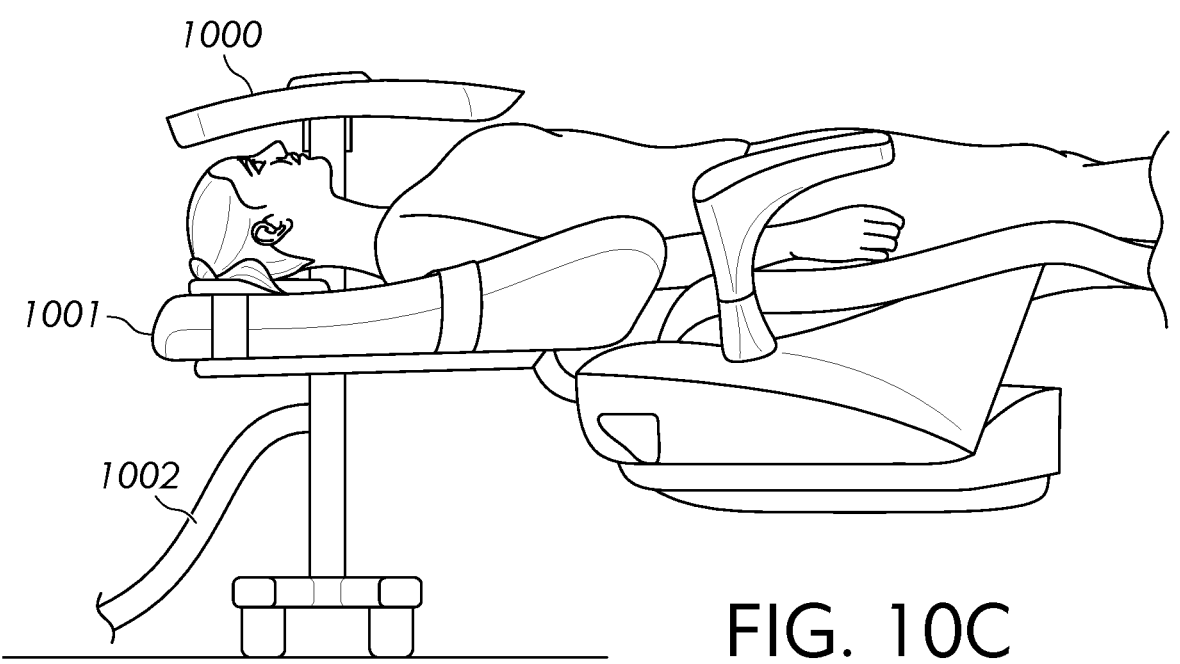
FIG. 10C is a side elevation view of a system of the present disclosure wherein a patient is occupying a dental chair as contemplated by the present disclosure and wherein the suctioning component of the system is mounted to a wall adjacent to a dental chair occupied by a patient.
Figure 11A:
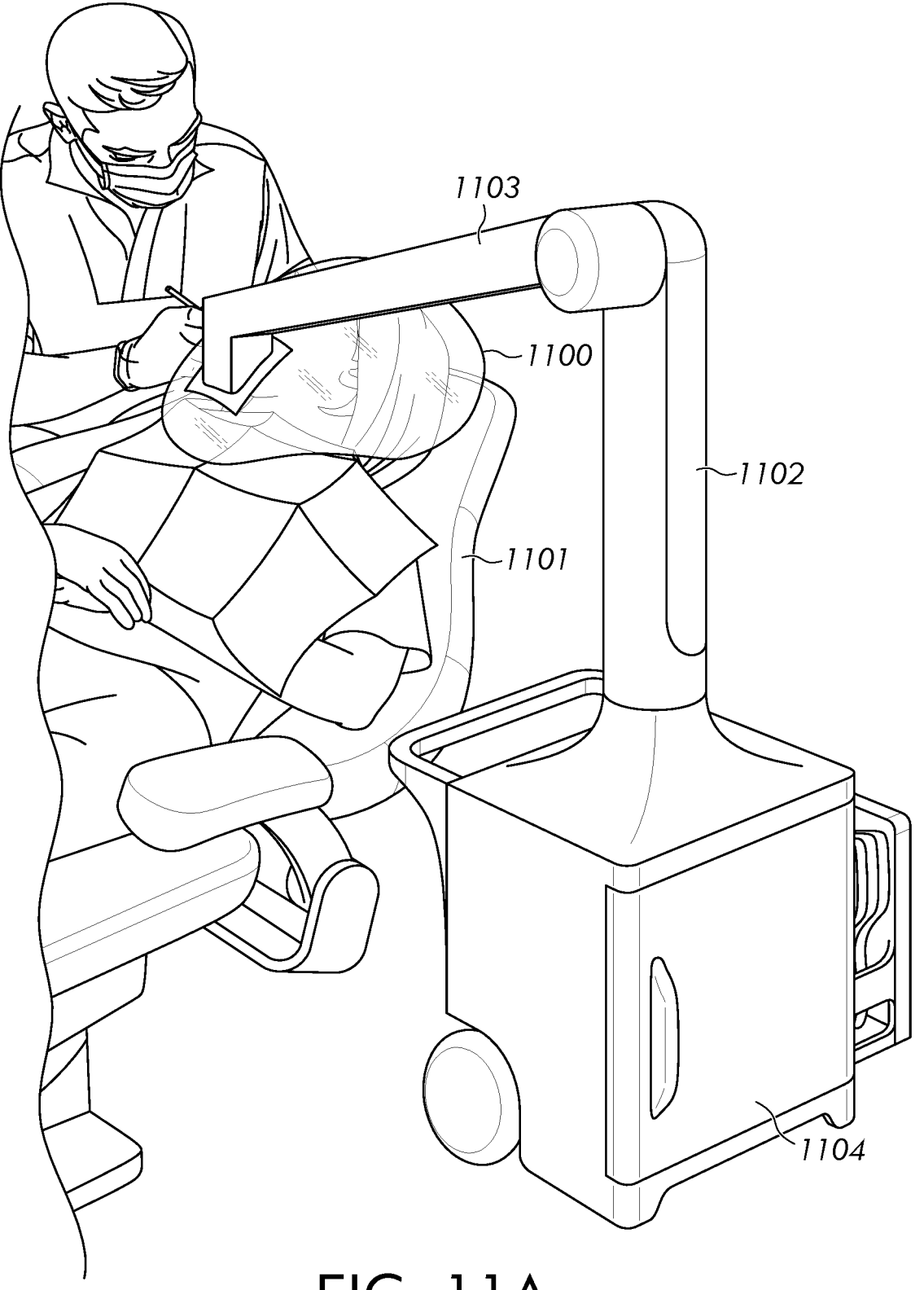
FIG. 11A is a perspective view of a system of the present disclosure wherein a patient is occupying a dental chair as contemplated by the present disclosure and wherein the components of the system are integrated into a single unit.
Figure 11B:
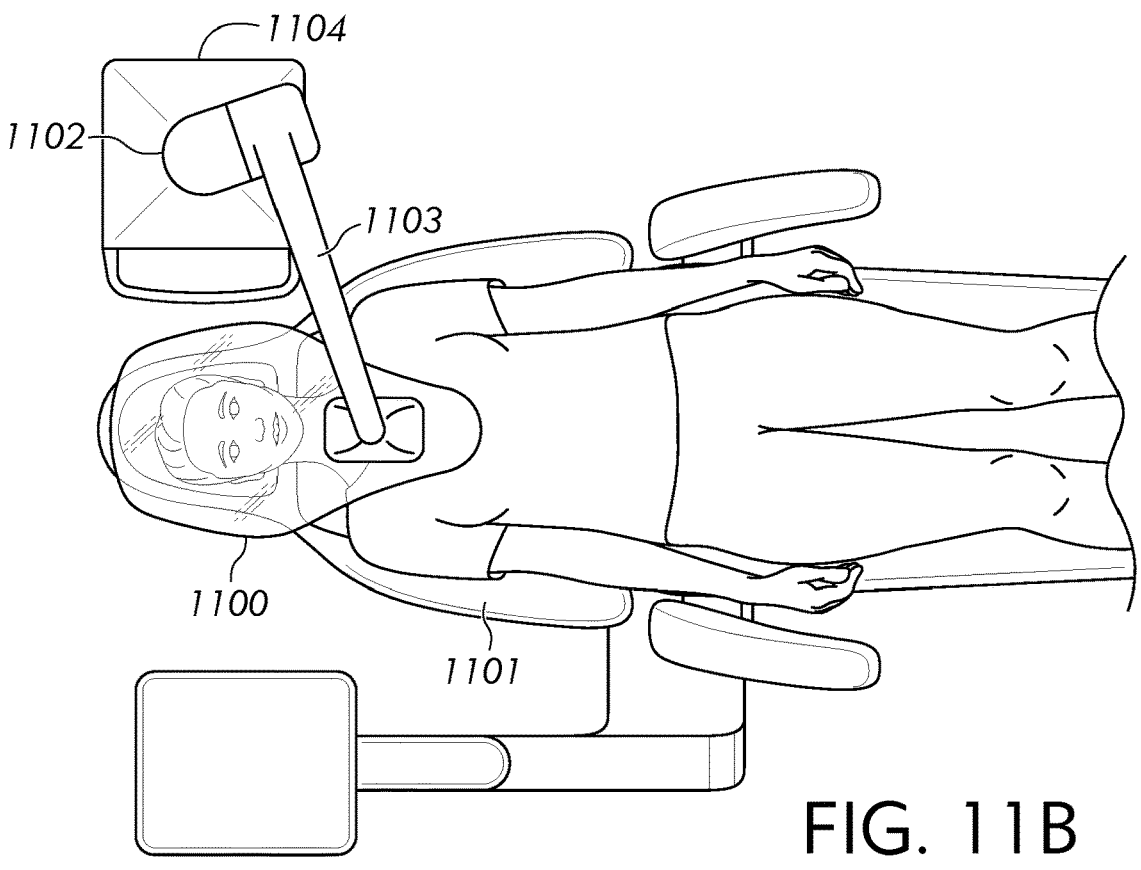
FIG. 11B is a top view plan of a system of the present disclosure wherein a patient is occupying a dental chair as contemplated by the present disclosure and wherein the components of the system are integrated into a single unit.
Figure 11C:
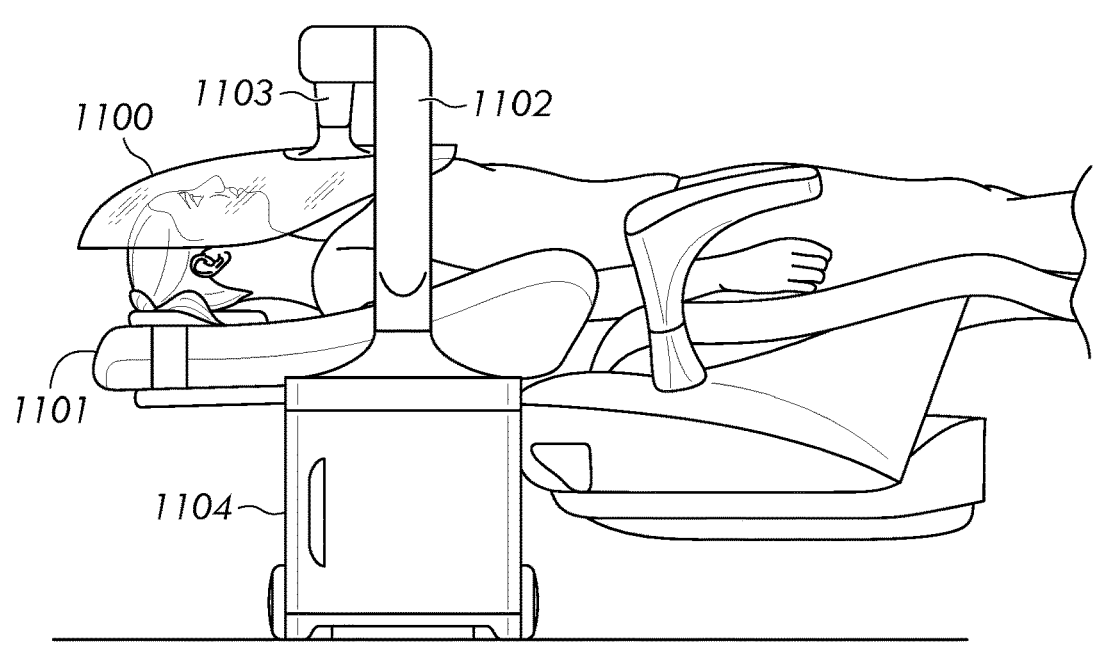
FIG. 11C is a side elevation view of a system of the present disclosure wherein a patient is occupying a dental chair as contemplated by the present disclosure and wherein the components of the system are integrated into a single unit.
Figure 12A:
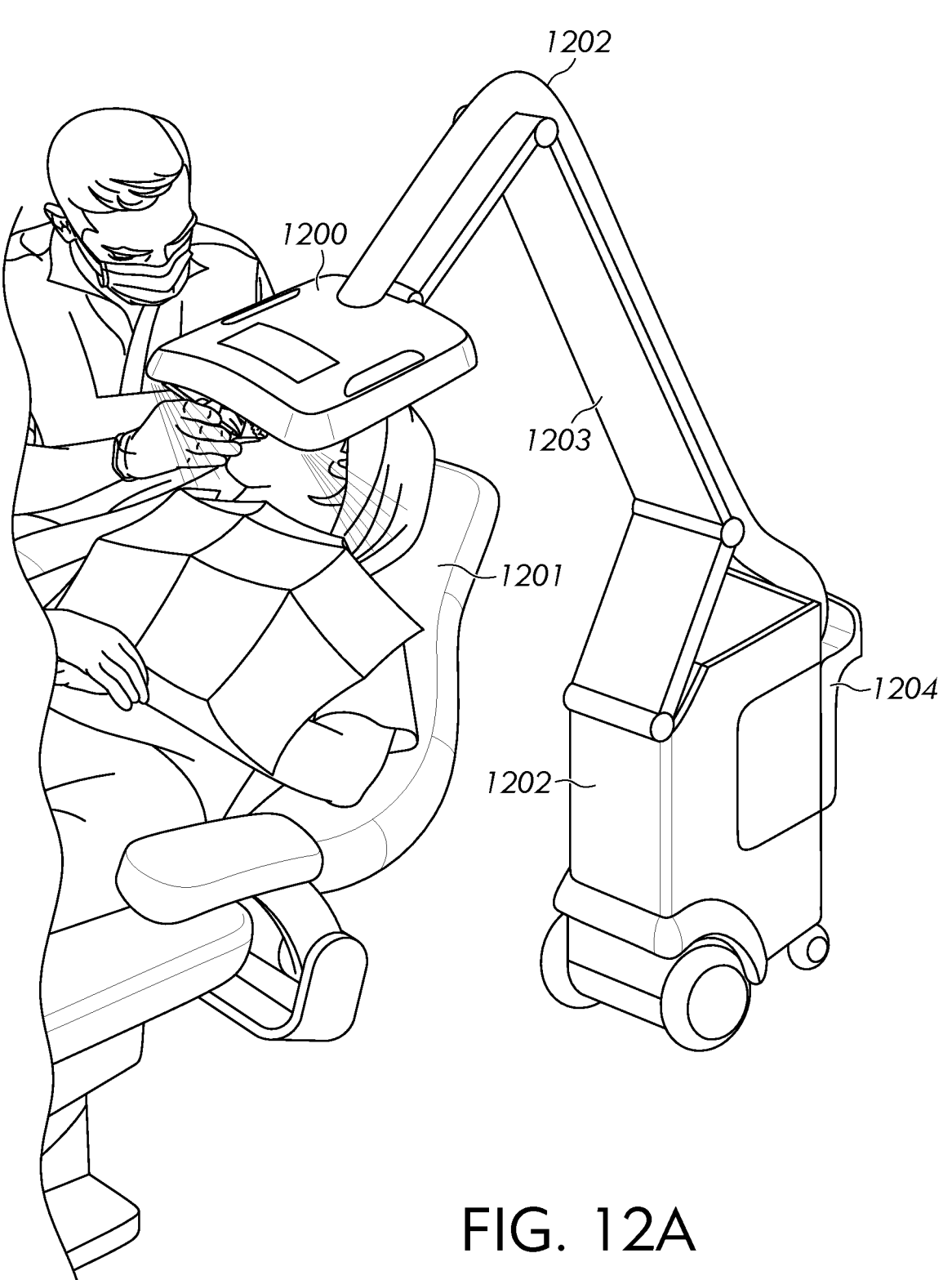
FIG. 12A is a perspective view of a system of the present disclosure wherein a patient is occupying a dental chair as contemplated by the present disclosure, wherein the components of the system are integrated into a single unit, and wherein the system further comprises a docking station for supplying power to said integrated unit.
Figure 12B:
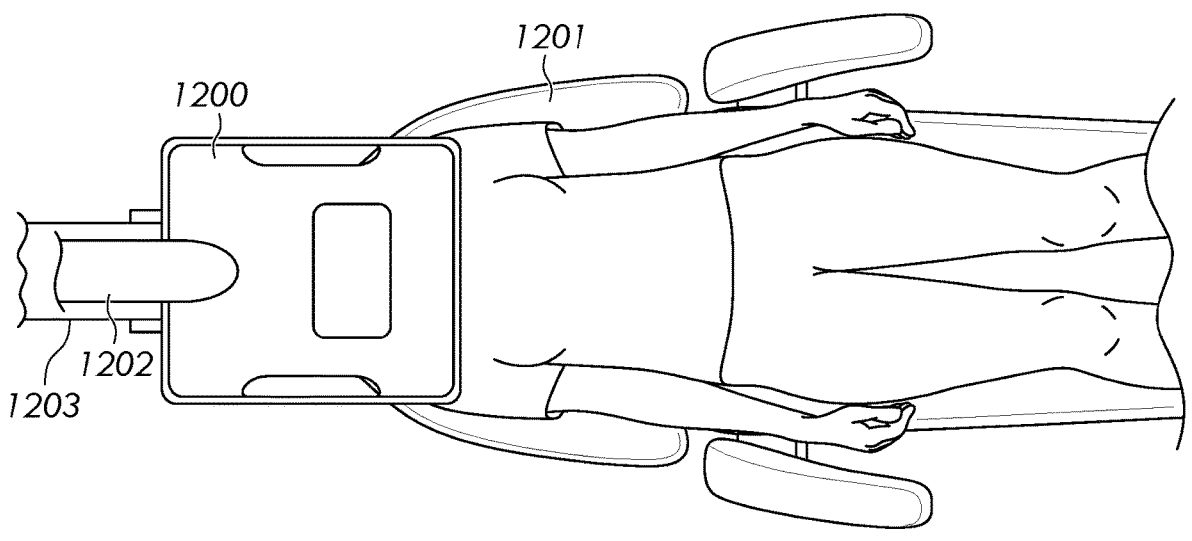
FIG. 12B is a top plan view of a system of the present disclosure wherein a patient is occupying a dental chair as contemplated by the present disclosure, wherein the components of the system are integrated into a single unit, and wherein the system further comprises a docking station for supplying power to said integrated unit.
Figure 12C:
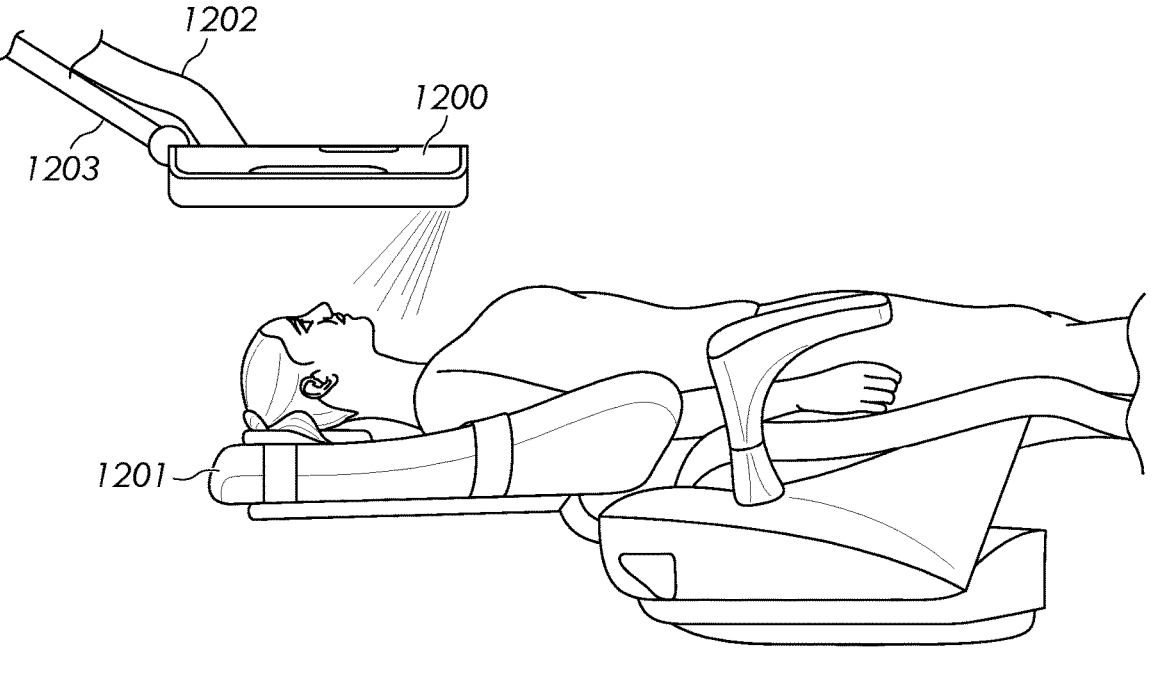
FIG. 12C is a side elevation view of a system of the present disclosure wherein a patient is occupying a dental chair as contemplated by the present disclosure, wherein the components of the system are integrated into a single unit, and wherein the system further comprises a docking station for supplying power to said integrated unit.
Figure 13A:
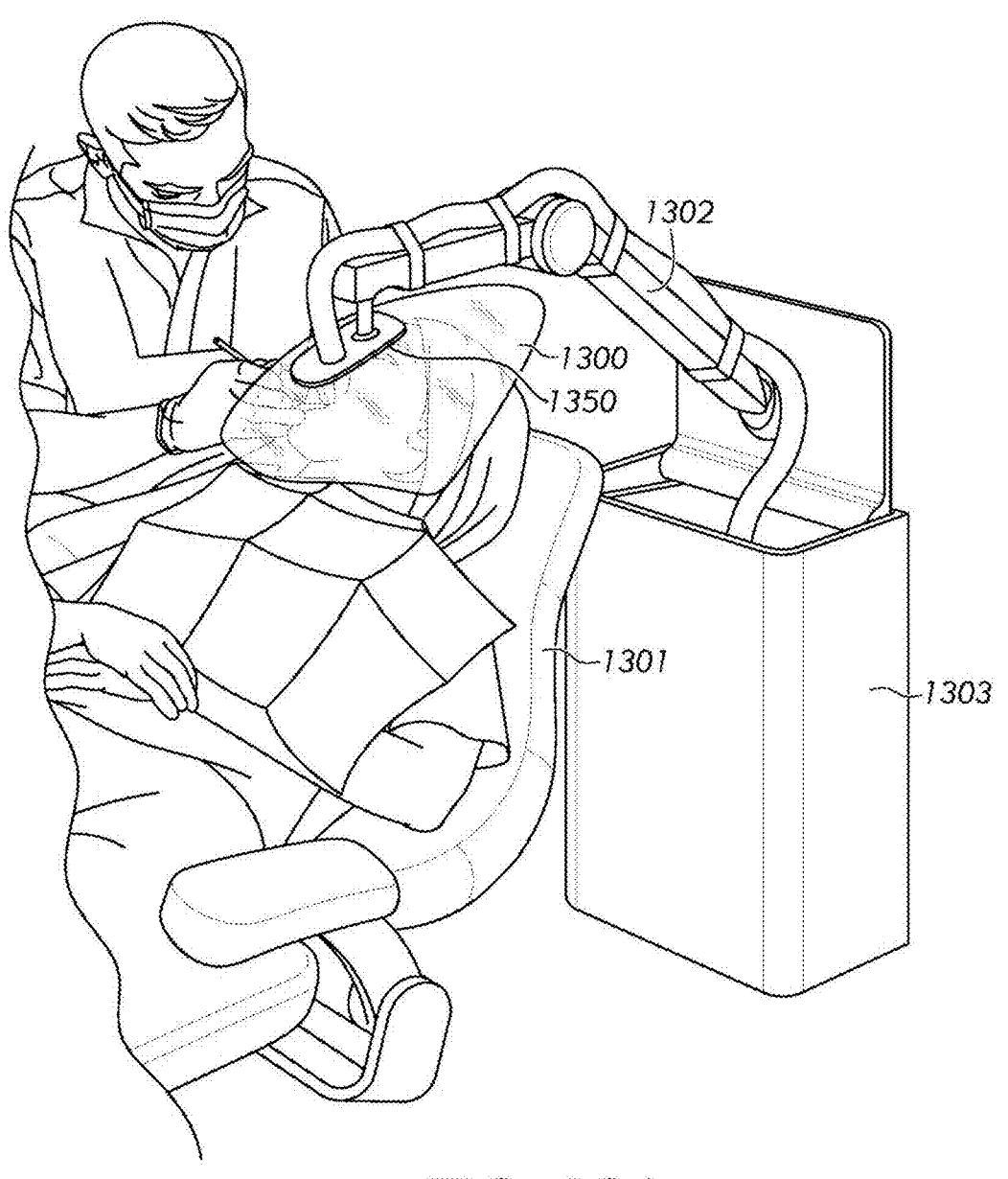
FIG. 13A is a perspective view of a system of the present disclosure wherein a patient is occupying a dental chair as contemplated by the present disclosure, wherein the components of the system are integrated into a unit mountable on a wall, and wherein the substantially transparent shield component extends from said unit via a collapsible arm.
Figure 13B:
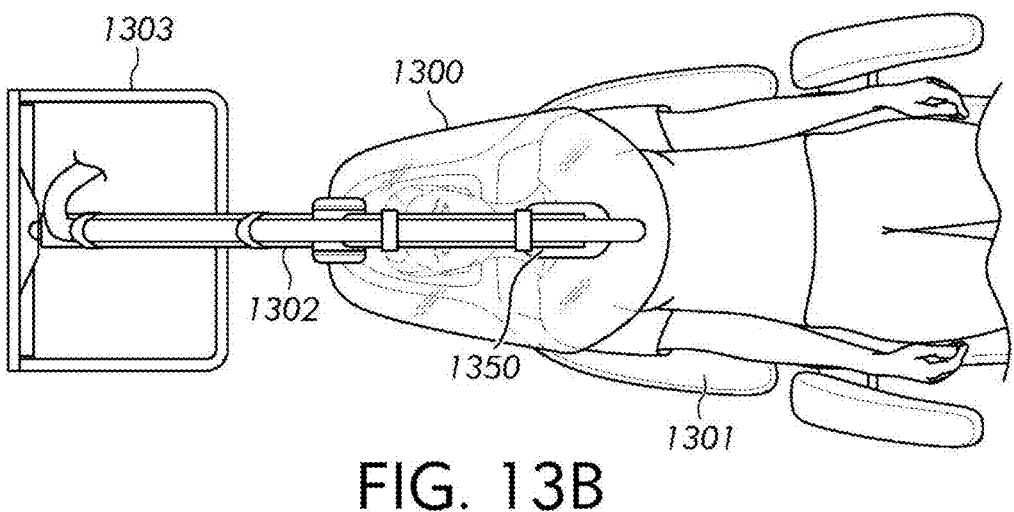
FIG. 13B is a top plan view of a system of the present disclosure wherein a patient is occupying a dental chair as contemplated by the present disclosure, wherein the components of the system are integrated into a unit mountable on a wall, and wherein the substantially transparent shield component extends from said unit via a collapsible arm.
Figure 13C:
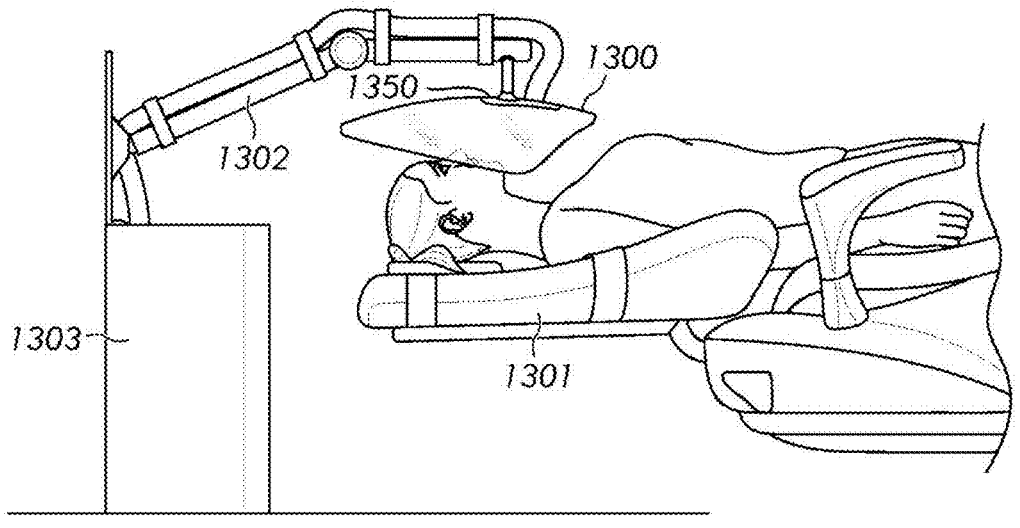
FIG. 13C is a side elevation view of a system of the present disclosure wherein a patient is occupying a dental chair as contemplated by the present disclosure, wherein the components of the system are integrated into a unit mountable on a wall, and wherein the substantially transparent shield component extends from said unit via a collapsible arm.
Figure 14A:
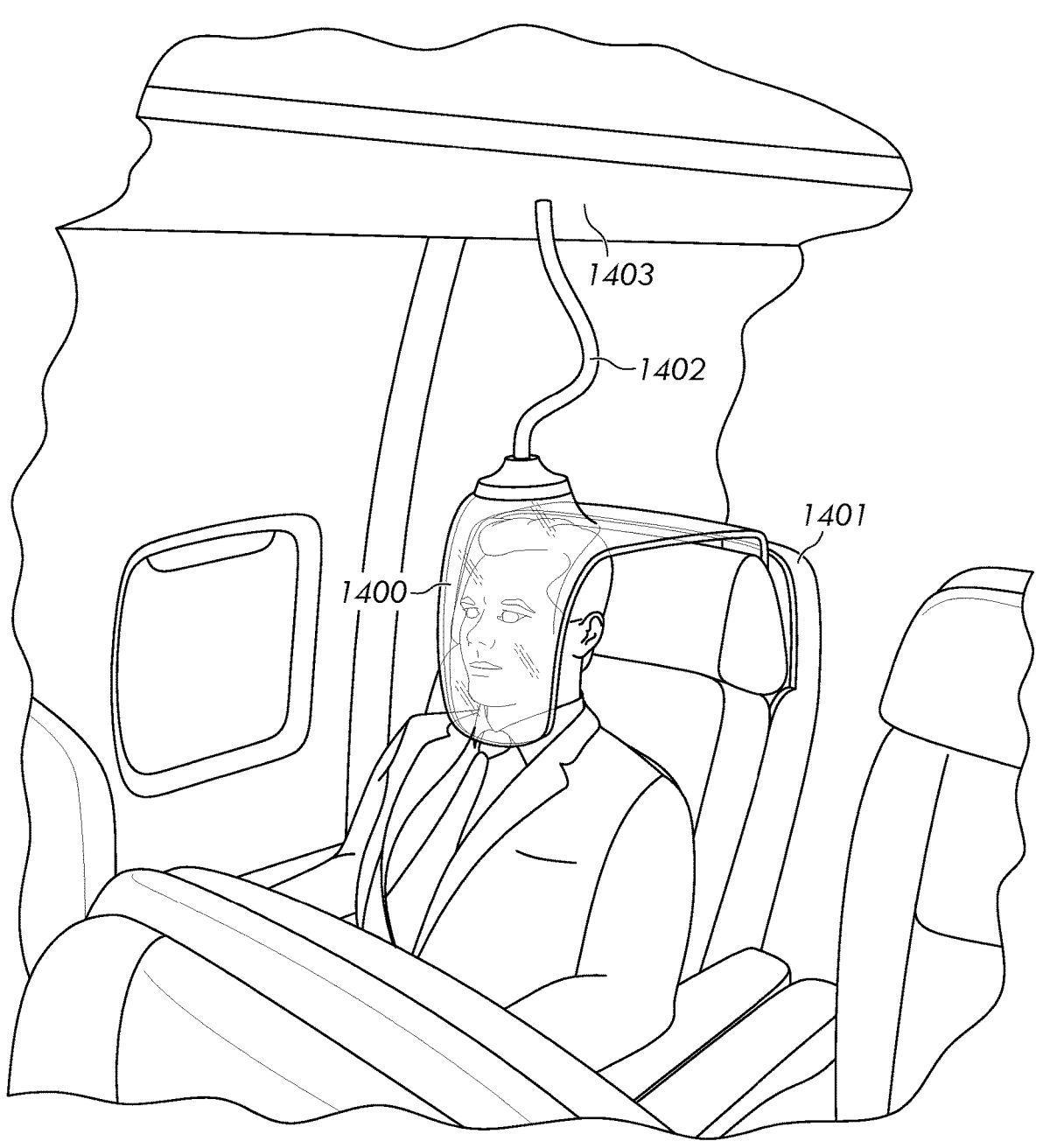
FIG. 14A is a perspective view of a system according to the present disclosure wherein the object contemplated by the system comprises a seat in an aircraft.
Figure 14B:
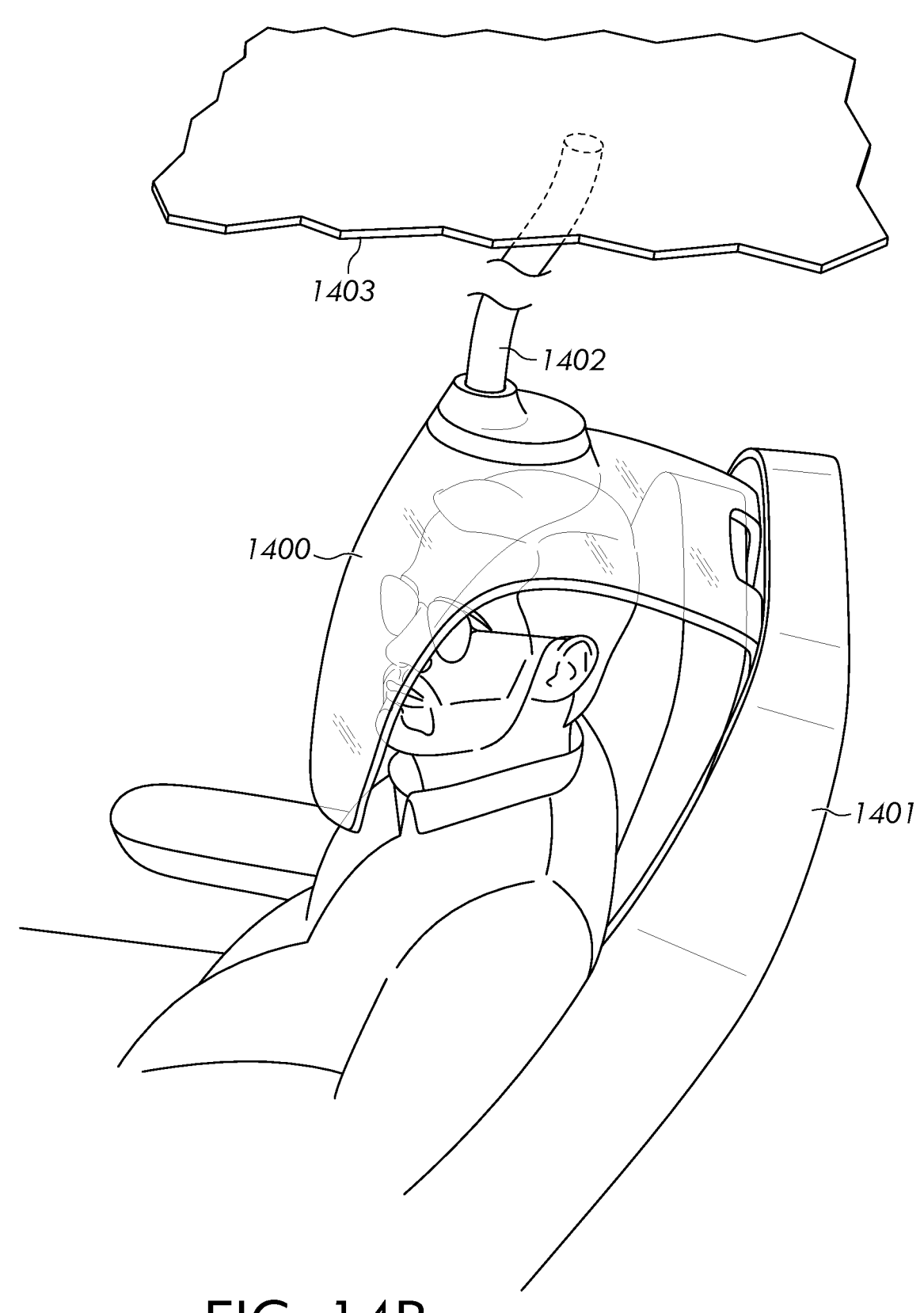
FIG. 14B is a side elevation view of a system according to the present disclosure wherein the object contemplated by the system comprises a seat in an aircraft.

Referring now to FIGS. 8A-8C, where the object is a dolly, the dolly may further comprise an upward extending aspect 803 that may be adjusted in height and may rotate around a horizontal axis. The base of the dolly may exist in any number of forms, including, without limitation, a tripod 804. According to such an embodiment, the base of the tripod may further be foldable.

The suctioning component of the systems of the present disclosure may comprise a freestanding unit 304, 403, 805, 903, 1102, 1202 or may be mountable to a wall 1003. The suctioning component may comprise a device capable of suctioning and thereby creating a vacuum. The suctioning component may comprise, without limitation, a High Energy Particular Air filter (i.e., a "HEPA" filter), a carbon filter, and/or another type of filter that would be appreciated by those of skill in the art after having the benefit of this disclosure.

Figure 3A:
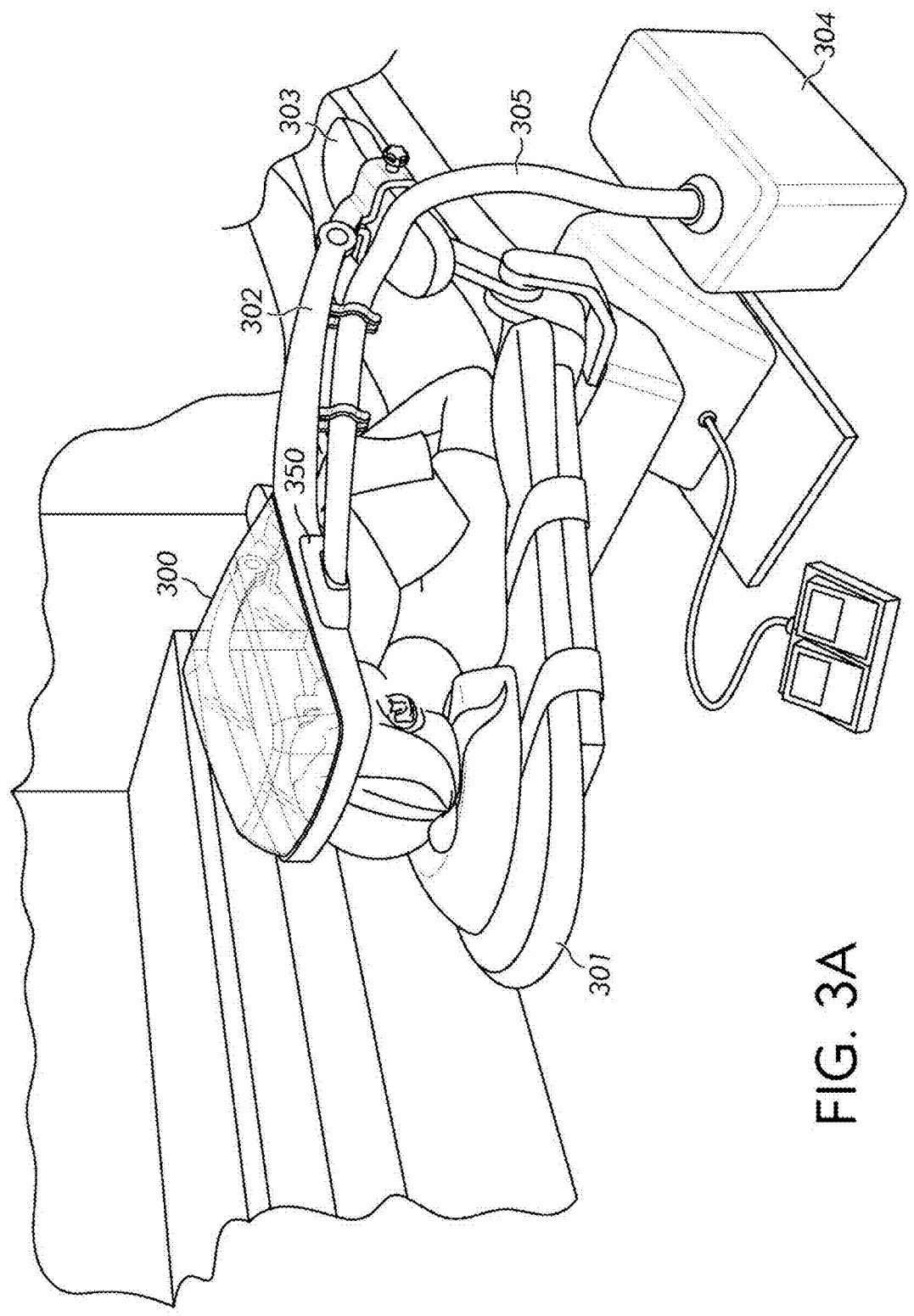
FIG. 3A is a perspective view of a system of the present disclosure wherein a patient is occupying a dental chair as contemplated by the present disclosure and wherein the substantially transparent shield component is attached to the dental chair by a rotatable arm attached to the arm rest of the dental chair.
Figure 3B:
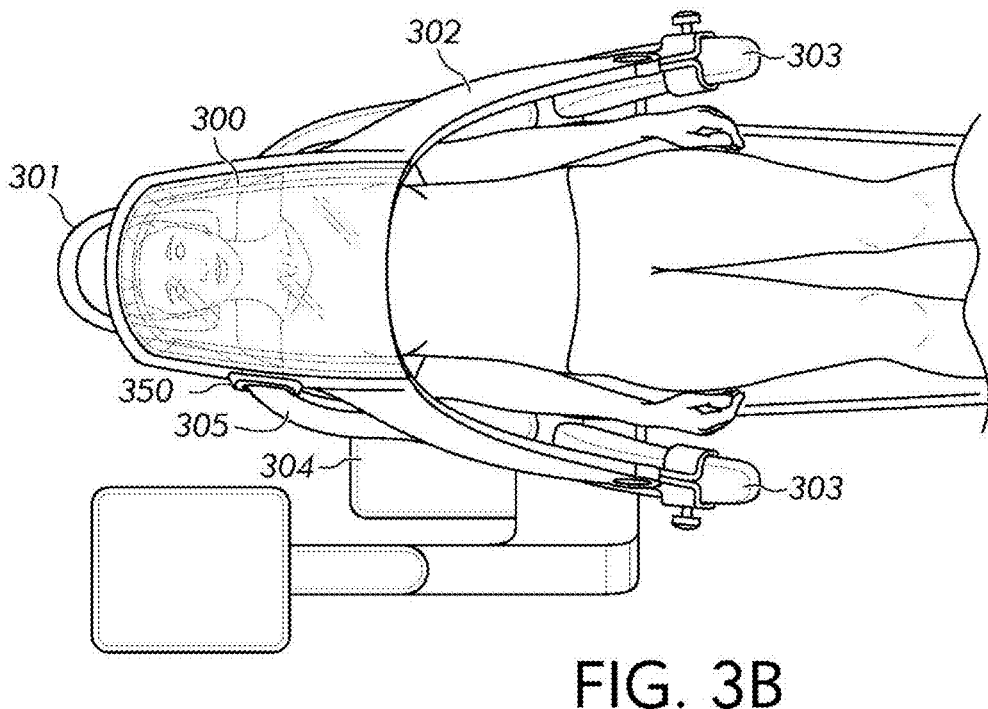
FIG. 3B is a top plan view of a system of the present disclosure wherein a patient is occupying a dental chair as contemplated by the present disclosure and wherein the substantially transparent shield component is attached to the dental chair by a rotatable arm attached to the arm rest of the dental chair.
Figure 3C:
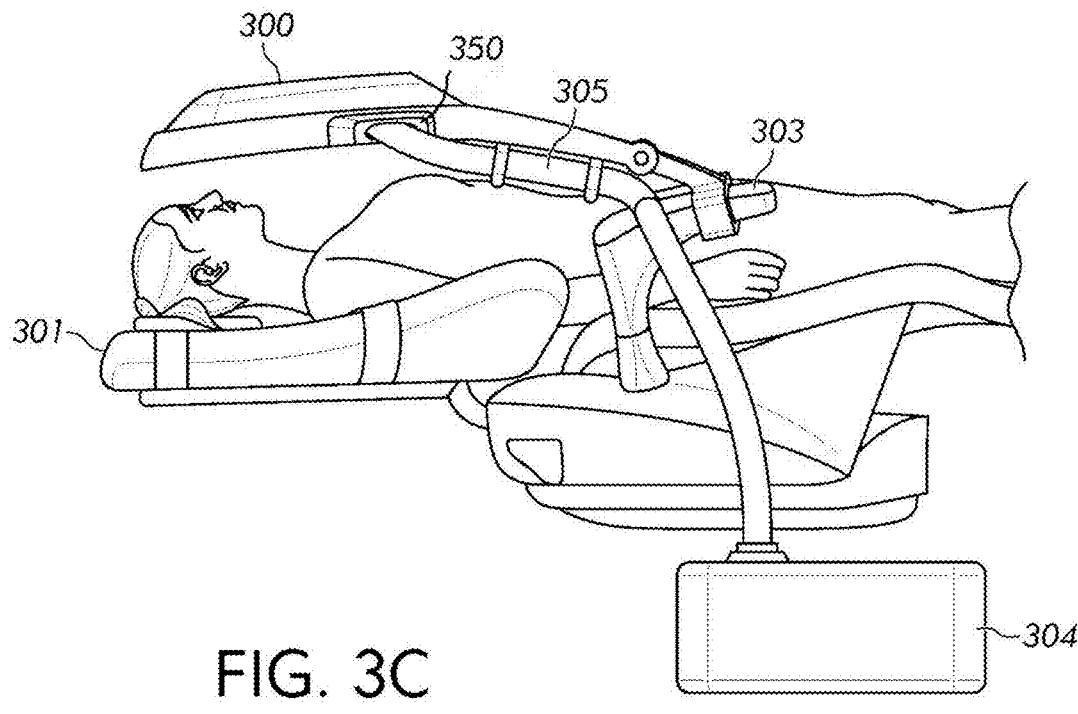
FIG. 3C is a side elevation view of a system of the present disclosure wherein a patient is occupying a dental chair as contemplated by the present disclosure and wherein the substantially transparent shield component is attached to the dental chair by a rotatable arm attached to the arm rest of the dental chair.

As reflected in FIGS. 3A-3C, the suctioning component may comprise a hose 305 connected to the shield component 300 of the system of the present disclosure.

Figure 4A:
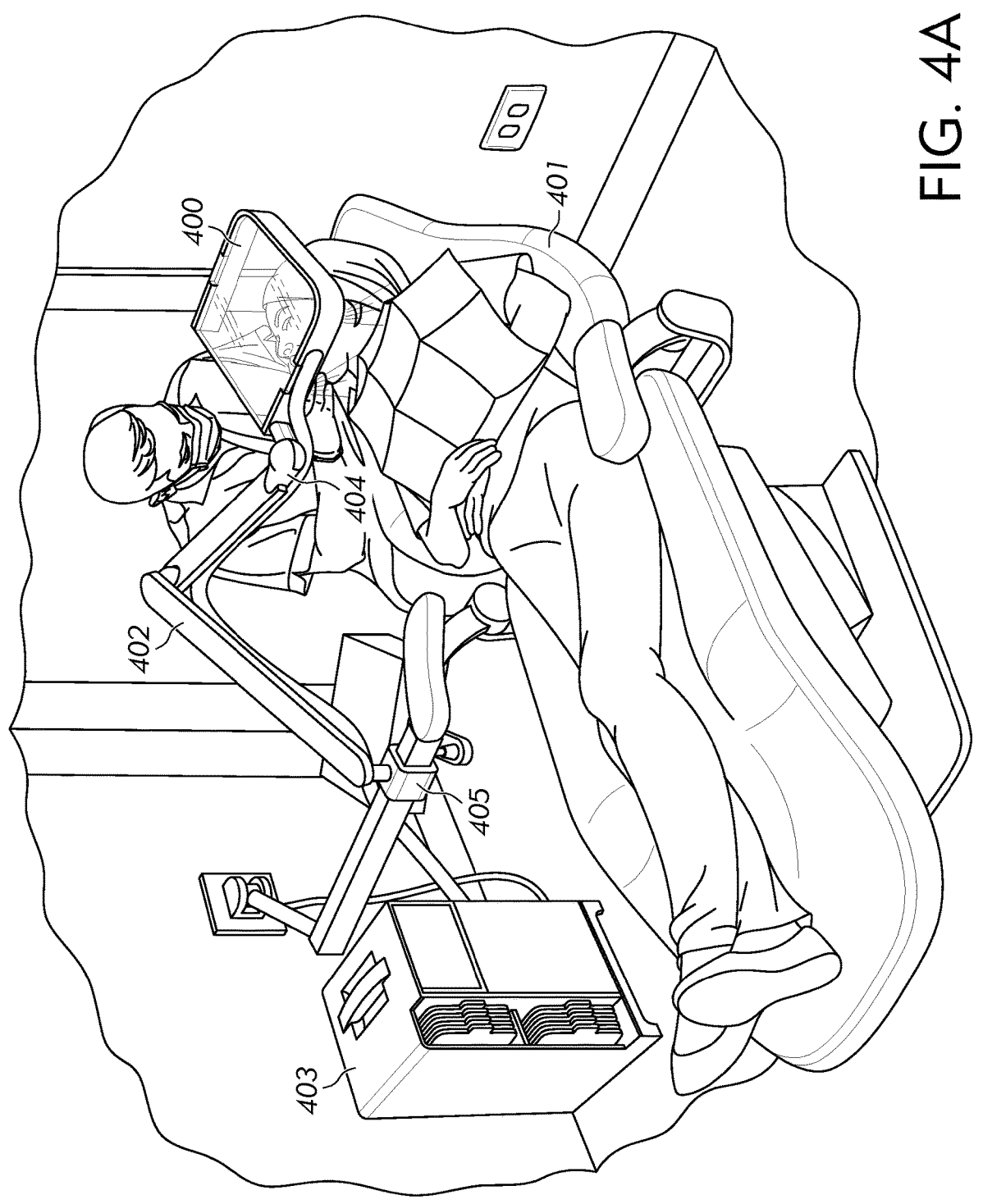
FIG. 4A is a perspective view of a system of the present disclosure wherein a patient is occupying a dental chair as contemplated by the present disclosure and wherein the substantially transparent shield component is integrated into a dental tray.
Figure 4B:
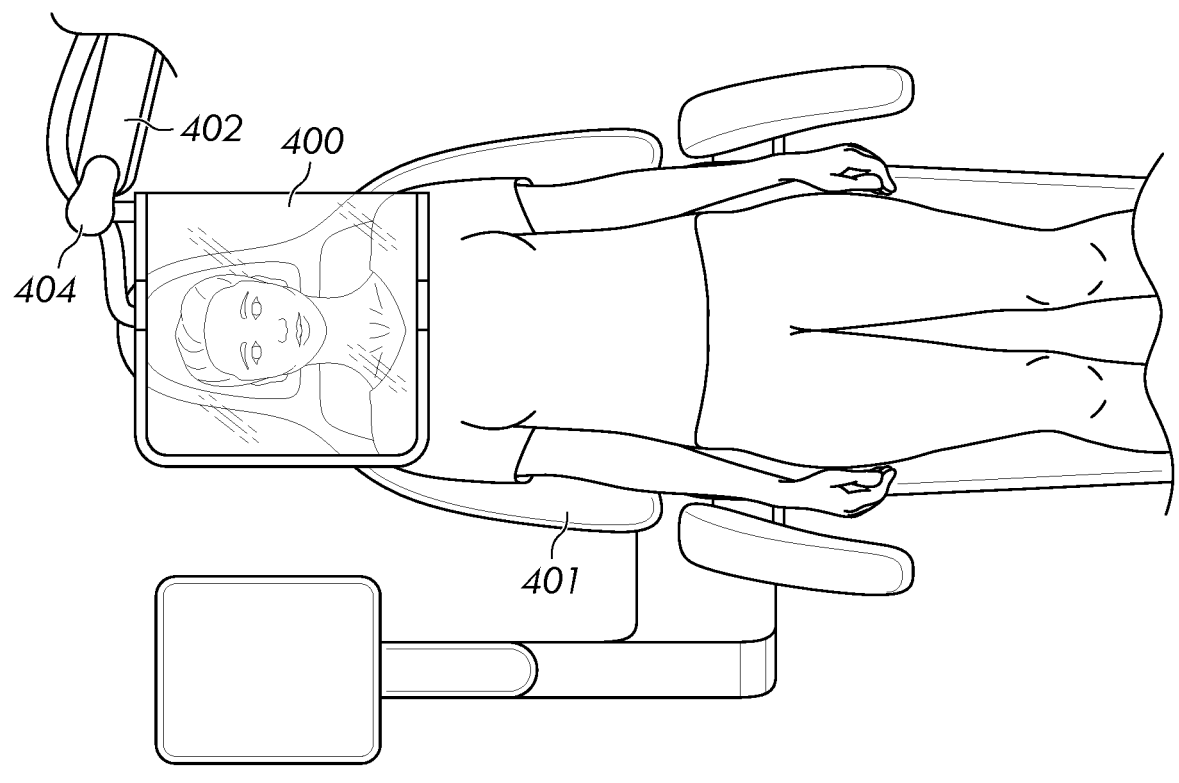
FIG. 4B is a top plan view of a system of the present disclosure wherein a patient is occupying a dental chair as contemplated by the present disclosure and wherein the substantially transparent shield component is integrated into a dental tray.
Figure 4C:
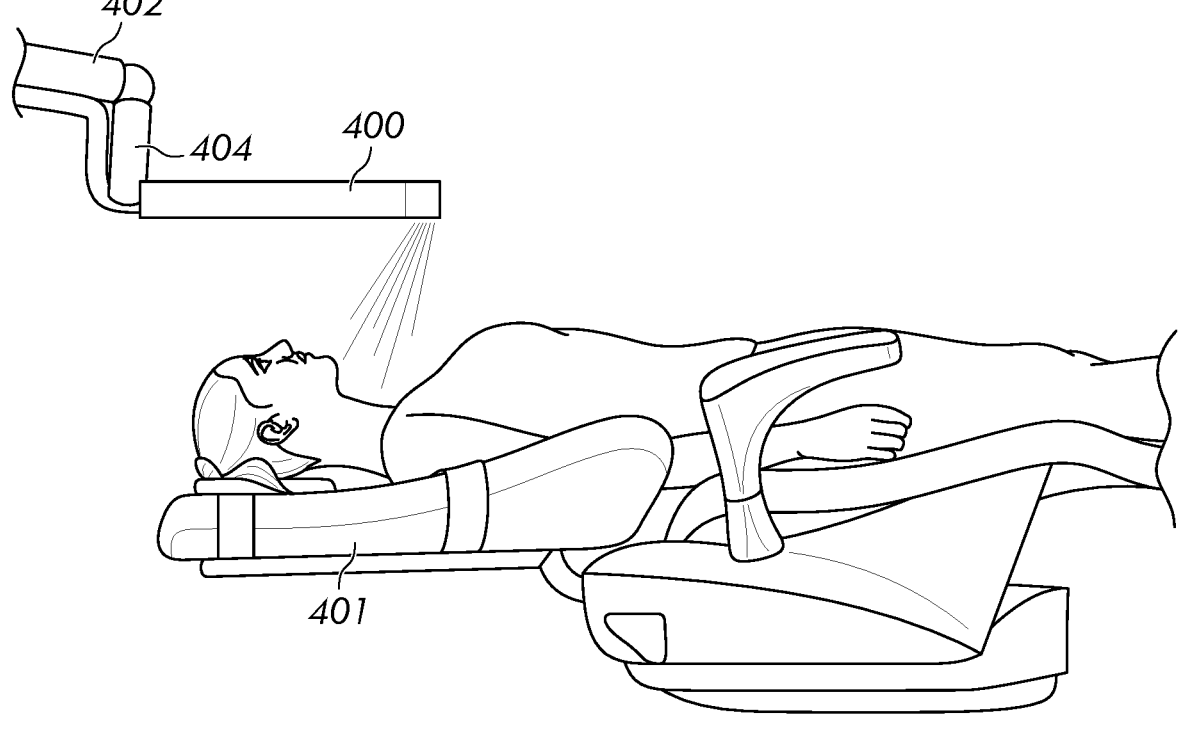
FIG. 4C is a side elevation view of a system of the present disclosure wherein a patient is occupying a dental chair as contemplated by the present disclosure and wherein the substantially transparent shield component is integrated into a dental tray.
Figure 5A:
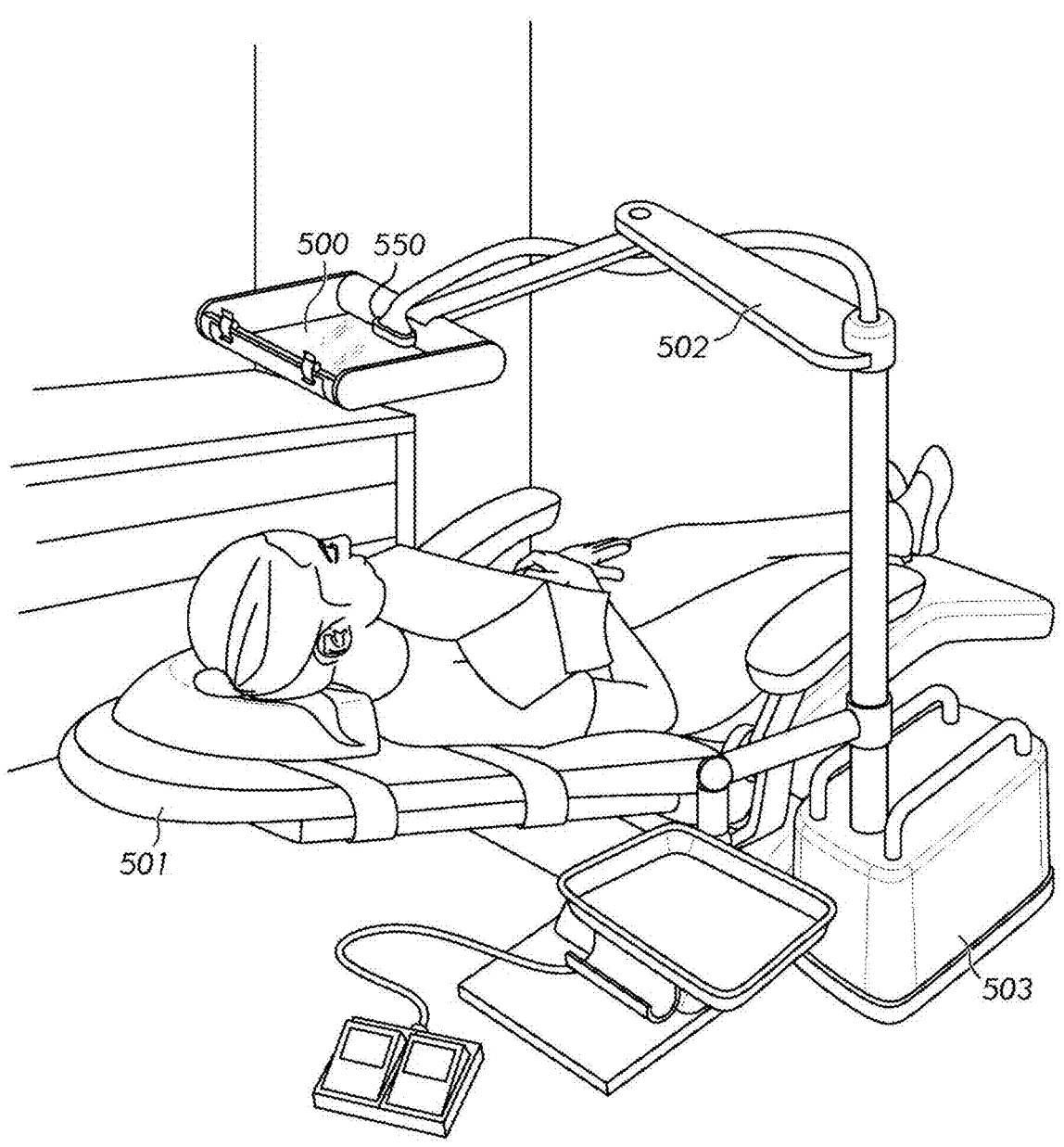
FIG. 5A is a perspective view of a system of the present disclosure wherein a patient is occupying a dental chair as contemplated by the present disclosure and wherein the components of the system are integrated into a single unit attachable to the base of the dental chair.
Figures 5B, 5C:
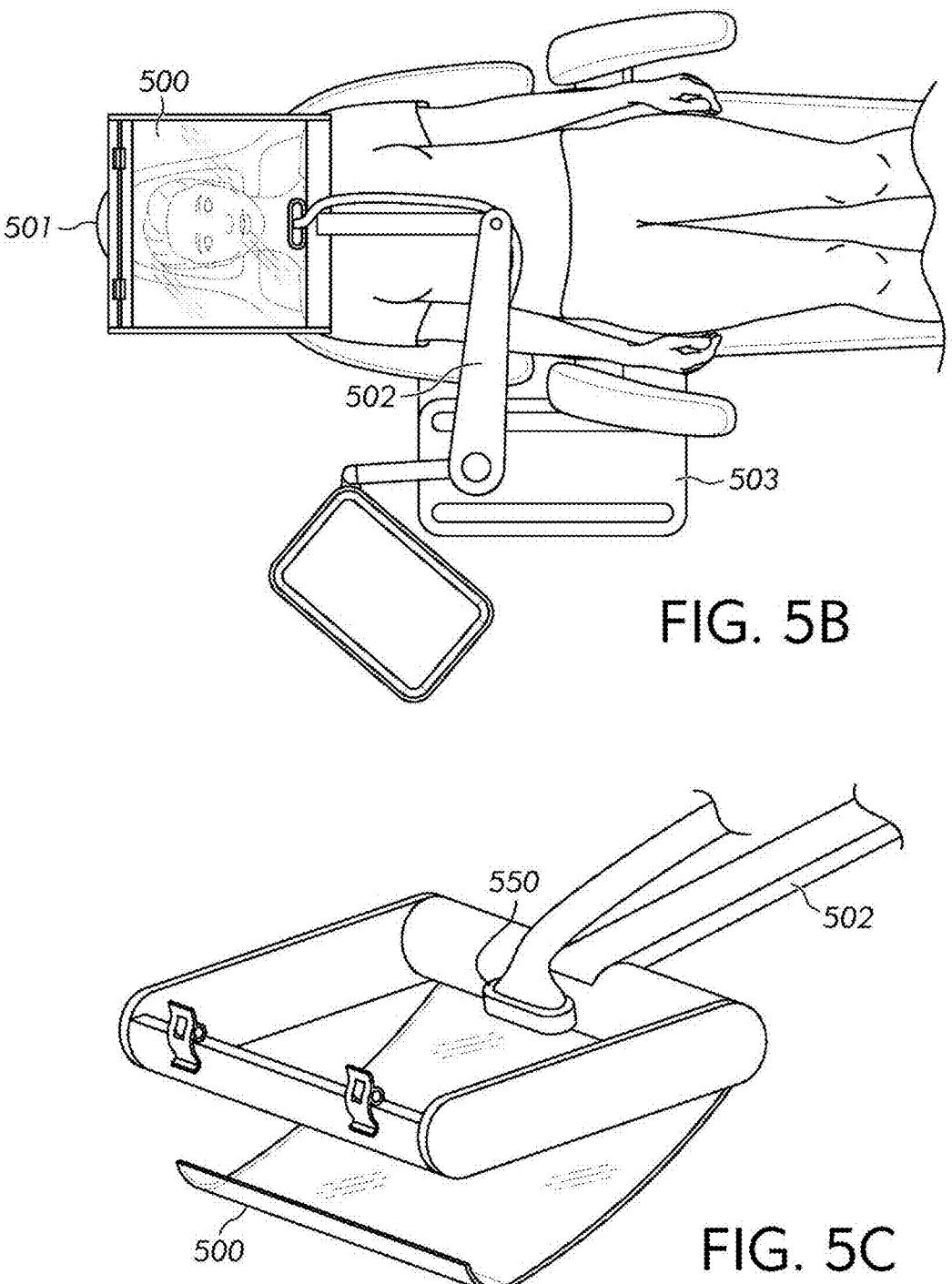
FIG. 5B is a top plan view of a system of the present disclosure wherein a patient is occupying a dental chair as contemplated by the present disclosure and wherein the components of the system are integrated into a single unit attachable to the base of the dental chair.
FIG. 5C is a perspective view of a substantially transparent shield component as contemplated by the present disclosure wherein the shield component comprises removable substantially transparent sheets.
Figure 6A:
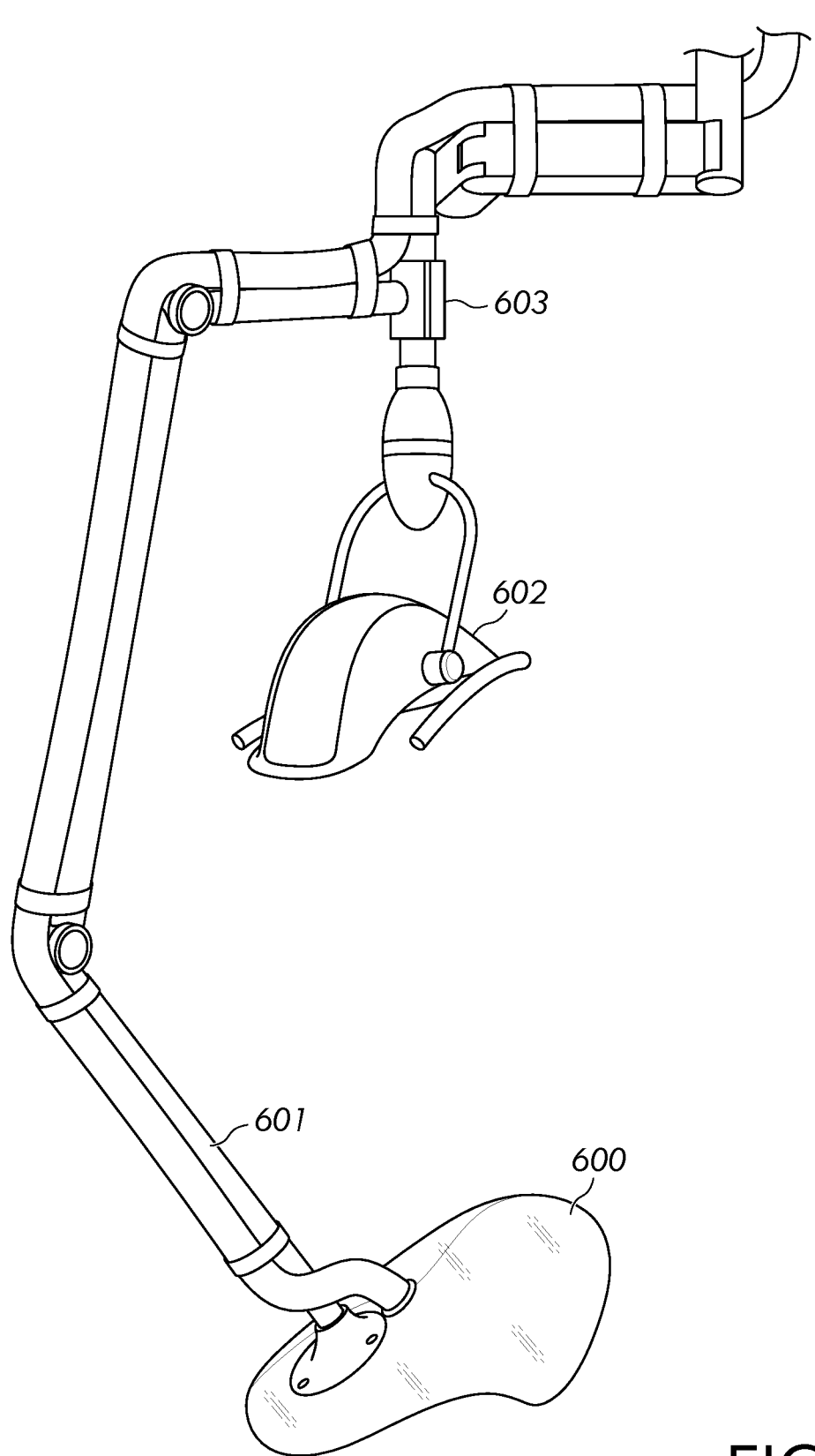
FIG. 6A is a perspective view of a system of the present disclosure wherein a patient is occupying a dental chair as contemplated by the present disclosure and wherein the substantially transparent shield component extends over the patient from a ceiling over top of the patient and extends alongside an existing dental lamp.
Figure 6B:
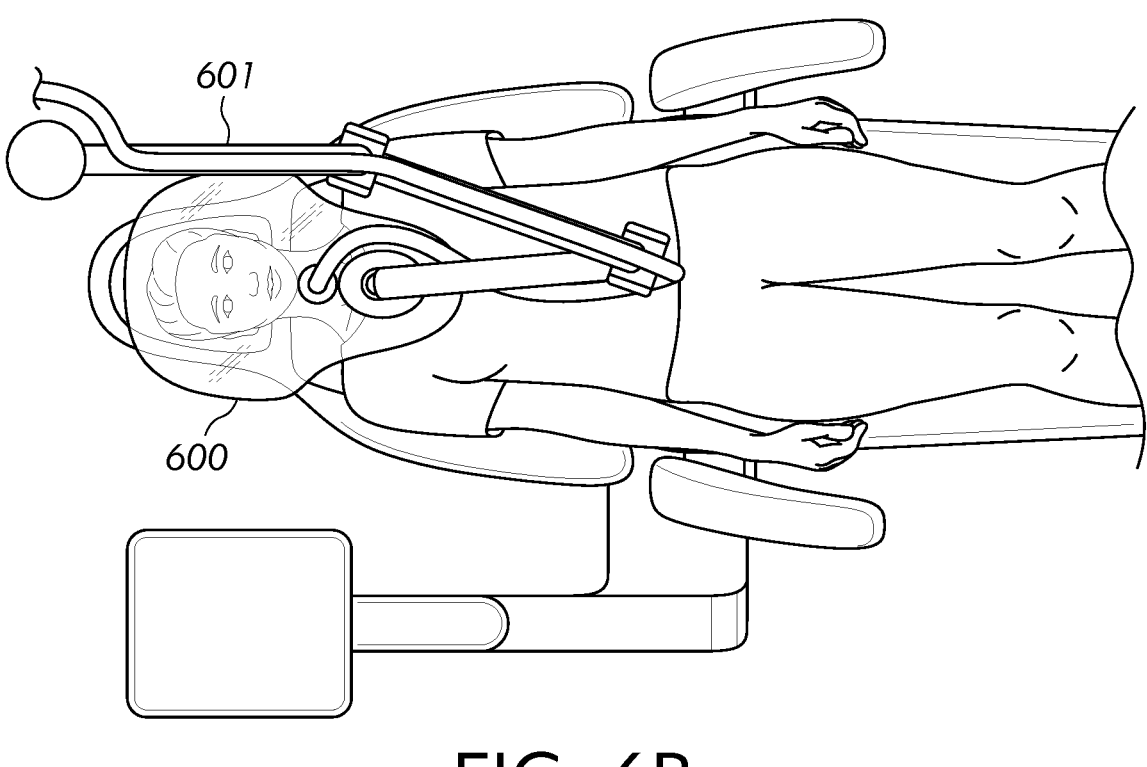
FIG. 6B is a top plan view of a system of the present disclosure wherein a patient is occupying a dental chair as contemplated by the present disclosure and wherein the substantially transparent shield component extends over the patient from a ceiling over top of the patient and extends alongside an existing dental lamp.
Figure 6C:
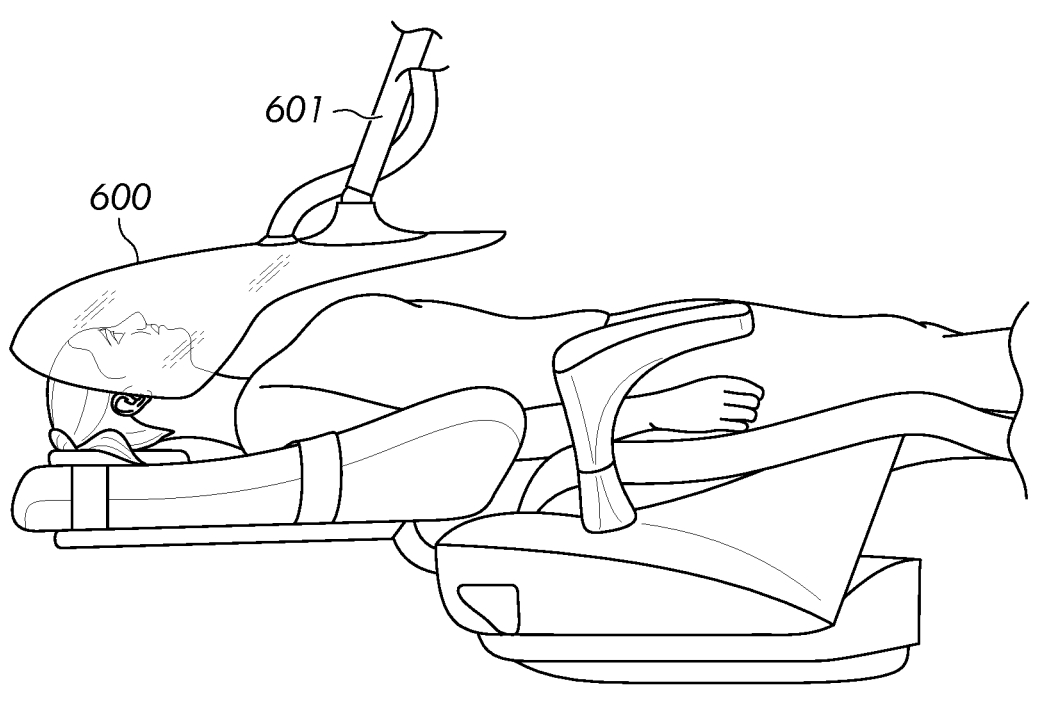
FIG. 6C is a side elevation view of a system of the present disclosure wherein a patient is occupying a dental chair as contemplated by the present disclosure and wherein the substantially transparent shield component extends over the patient from a ceiling over top of the patient and extends alongside an existing dental lamp.
Figures 7A, 7B:
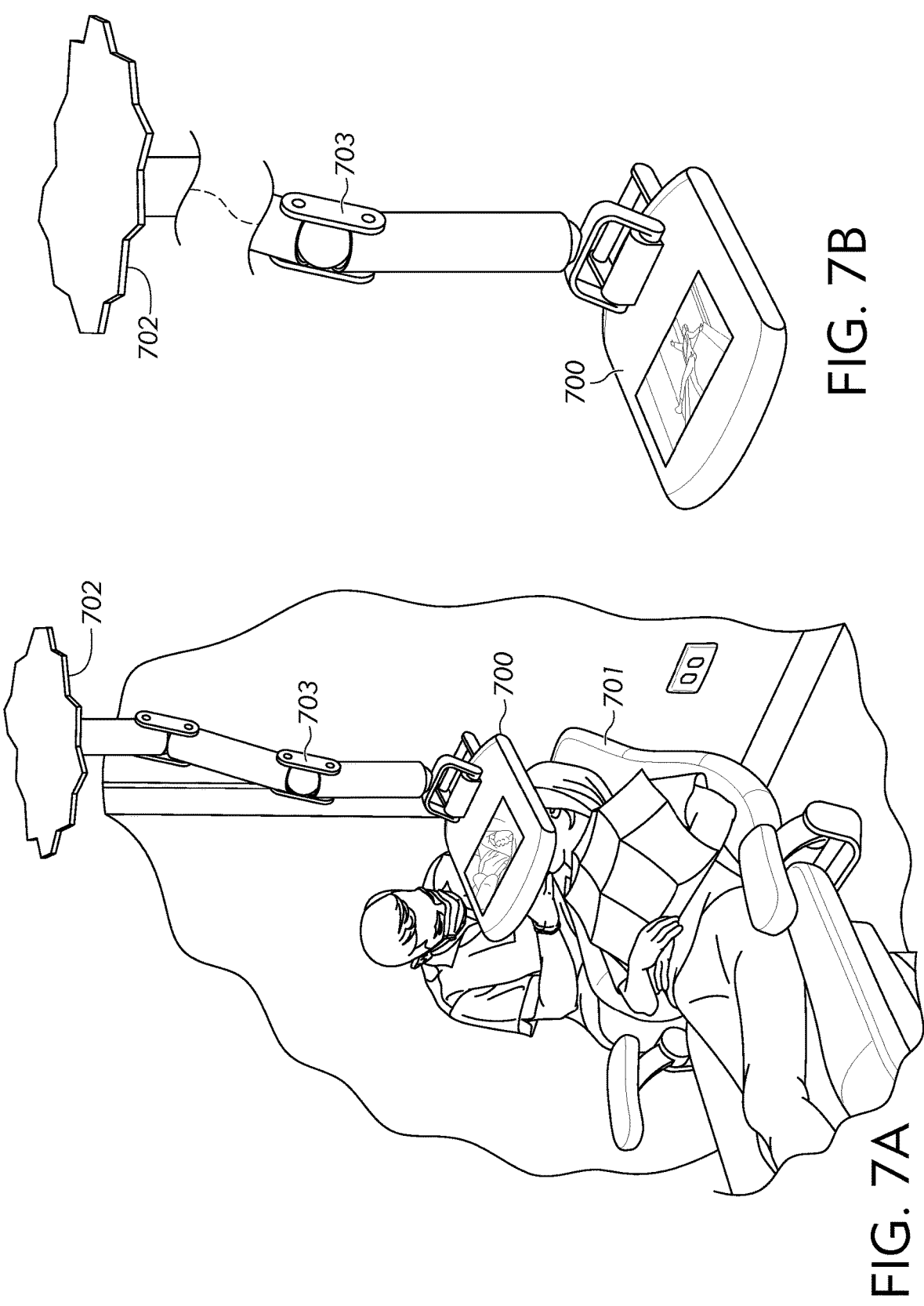
FIG. 7A is a perspective view of a system of the present disclosure wherein a patient is occupying a dental chair as contemplated by the present disclosure and wherein the substantially transparent shield component is mounted to and extends downward from a ceiling over top of a patient occupying the dental chair wherein the substantially transparent shield component includes LED lighting, magnifying capability, and, optionally, a screen capable of delivering entertainment or other media content to the patient.
FIG. 7B is a perspective view of a substantially transparent shield component as depicted in FIG. 7A.

Referring now to FIGS. 4A-4C, the substantially transparent shield component of the system of the present disclosure may form a dental tray. According to such an embodiment, the dental tray may further comprise light emitting diodes located around the frame of the tray to enhance visibility of a dentist performing dental work on a patient occupying the dental chair. According to such an embodiment, the substantially transparent shield component/dental tray may be replaceable. According to such an embodiment, the substantially transparent shield component/dental tray may be washable. According to such an embodiment, the substantially transparent shield component/dental tray may be connected to the arm of the dental chair by means of, without limitation, an extendable/collapsible connecting aspect comprising a ball joint 404 operatively attached to the substantially transparent shield component/dental tray.

Referring now to FIGS. 6A-6C and 7A-7B, the substantially transparent shield component of the present disclosure may be operatively attached to a ceiling 702 and may extend downward from said ceiling. According to such embodiment, in the case of a dentist's office, the arm 601, 703 associated with the substantially transparent shield component may be connected to, and extend alongside, a dental lamp 602. According to such an embodiment, the arm associated with the substantially transparent shield component may be connected to the dental lamp via a universal mount 603.

The system of the present disclosure may comprise a fully integrated unit 503, 1102, 1202, 1303, comprising the sub-stantially transparent shield component, chamber component, and suctioning component. Said fully integrated unit may be mountable on a wall 1003. Said integrated unit may further comprise storage for replacement substantially transparent shields 1104.

According to an embodiment of the present disclosure, the system of the present disclosure may draw upon a docking apparatus 1204 for power.

The substantially transparent shield component may be comprised of any substantially transparent solid material such as, without limitation, certain types of plastic or clear glass. In one embodiment, the shield component may be constructed using materials that are not toxic to human beings. The plastics that may be suitable for use in preparing the shield component may comprise, without limitation, polymethyl methacrylate, cellulose acetate butyrate, polycarbonate, or glycol modified polyethylene terephthalate. Preferably, the shield component may be comprised of a light-weight material to facilitate contracting and expanding of the shield component toward or away from the front surface of the object and the patient or other individual occupying the object.

When in use, the shield component is intended to be positioned close to but not in contact with an individual sitting in the chair or otherwise occupying the object. In a preferred embodiment, said distance between the interior portion of the shield component and the individual occupying the object may be approximately one inch, without limitation. In another preferred embodiment, said distance between the interior portion of the shield component and the individual occupying the object may be approximately ten inches, without limitation. Other distances between the interior surface of the shield component and the individual that allow for the individual remaining sufficiently comfortable are intended to be included within the scope of this disclosure, as would be appreciated by those having skill in the art.

The shield component of the present disclosure may exist in virtually any number of dimensions. In one illustrative embodiment, the shield component may be approximately three feet to approximately six feet in length, preferably from approximately four feet to approximately four feet, six inches in length, without limitation. The shield component may preferably be constructed of a lightweight material to facilitate movement of the shield toward and away from the object and an individual occupying said object. The shield component may be approximately one foot, six inches, to approximately three feet in width, preferably from approximately two feet to approximately two feet, six inches in width, without limitation.

The substantially transparent shield component may contain material on each side that extends from the surface of the shield component toward the object so as to partially or fully enclose an occupant of the object. Such embodiments of the shield component of the present disclosure may further comprise an aperture on each side to allow, for example, for a dentist or dental assistant to perform dental work on a patient occupying a patient chair while the shield component is in the collapsed position. Alternatively, such extensions on the sides of the shield component may be omitted thereby further increasing accessibility to the occupant of the chair or other object.

The system of the present disclosure further comprises a chamber component. The chamber component 350, 550, 850, and 1350 may be operatively attached to the suctioning component. Said chamber component may, without limitation, be located approximately two-thirds of the distance from the distal end of the substantially transparent shield component to the proximal end of said component. The location of said chamber component 350, 550, 850, and 1350 may approximate the location of the mouth and nasal regions of an individual occupying the object over which the shield component has been placed.

The chamber component 350, 550, 850, and 1350 may extend to an aperture, which may be located at the distal end of the shield component. The chamber component of the systems of the present disclosure may further comprise diodes emitting ultraviolet light capable of disinfecting aerosols entering the chamber component from the space between the interior surface of the shield component and an object.

Systems of the present disclosure further comprise a suctioning component such as a vacuum wherein said suctioning component may suction air from the space between the interior surface of the shield component and the front of an individual occupying an object as contemplated by the present disclosure. The movement of air away from the individual occupying the object toward the suctioning component optionally may be further facilitated by a component capable of exerting pressure upon the air so as to propel the air forward toward the suctioning component.

The chamber component 350, 550, 850, and 1350 of the systems of the present disclosure may further comprise diodes emitting ultraviolet light capable of disinfecting aerosols entering the chamber component from the space between the interior surface of the shield component and the front of an individual occupying the object.

The systems of the present disclosure may further comprise supplemental lighting to enhance visibility for, for example, a dentist or dental assistant performing dental work inside the mouth of a patient occupying a dental chair as contemplated by this disclosure. Said supplemental lighting may be located, without limitation, on the interior of the substantially transparent shield component.

As discussed herein, the systems of the present disclosure may further comprise magnifying materials, such as, without limitation, magnifying glass, light emitting diodes providing supplemental lighting, and/or a camera communicatively connected to, without limitation, a liquid crystal display, wherein said magnifying materials may be located within a portion of the shield component at a location intended to approximate where a patient's mouth may be. In one embodiment of the present disclosure, said location may be approximately two-thirds of the distance from the distal end of the shield component to the proximal end of the shield component.

In an embodiment of the systems enabled by the present disclosure, the shield component 1400 may be operatively attached to a seat in an aircraft 1401. According to such an embodiment, the shield component may be detachable. While, according to this embodiment, the structure and operation of the shield component of the present disclosure may be substantially identical to that discussed above, the suctioning component may comprise a hose 1402 extending from near the proximal end of the shield component in the head region of an individual occupying the aircraft seat to a ventilation system of the aircraft accessible in the portion of the roof of the interior of the aircraft 1403 located immediately above a passenger seat. Alternatively, said hose may extend from near the distal end of the shield component to the floor of the interior of the aircraft. According to this embodiment, the shield component may be detachable from the seat in the aircraft. According to this embodiment, the shield component may be so detached, without limitation, by actuating a release mechanism by, for example, pressing a button that may be located within an approximately 16 inch radius from the aircraft seat.

In another embodiment of a system enabled by the present disclosure, the substantially transparent shield component may be operatively attached to the front passenger seat of an automobile. While, according to this embodiment, the structure and operation of the shield component of the present disclosure may be substantially identical to that discussed above, the suctioning component may be easily portable and may fit within the console compartment of the automobile.

In another embodiment of a system enabled by the present disclosure, the substantially transparent shield component may be operatively attached to a bed such as, without limitation, a hospital bed. The shield component may be extended to approximately five feet to approximately eight feet in length, preferably from approximately six feet to approximately seven feet in length, without limitation. The shield component may be positioned to collapse toward the front of an individual lying in the bed. According to such an embodiment, the shield component may be designed so as to completely enclose the occupant of the bed. According to such an embodiment, the aperture through which air may be suctioned may be located at either end of the shield component.

While various aspects of the systems of this disclosure have been described above, the description of this disclosure is intended to illustrate and not limit the scope of the system. The invention is defined by the scope of the claims and not the illustrations and examples provided in the above disclosure. Skilled artisans will appreciate additional aspects of the systems enabled by this disclosure, which may be realized in alternative embodiments, after having the benefit of the above disclosure. Other aspects, advantages, embodiments, and modifications are within the scope of the claims.

What is claimed is:

1. A system for mitigating risk of transmission of an infectious disease comprising:

a shield component configured to at least partially surround an individual's head;

a chamber component comprising a structure defining a partially enclosed space configured to receive air or another gaseous material, wherein the chamber component further comprises light emitting diodes configured to exude disinfecting ultraviolet light, wherein the chamber component is configured to be positioned above a nasal and mouth region of the individual, and wherein the chamber component is attached to the shield component; and a suctioning component, being attached to the shield component and being operatively attached to the chamber component, comprising a negative air pressure pump for suctioning aerosol attached to an interior surface of said shield component out of a space between said shield component and an individual occupying a seat in an aircraft over which the shield component has been placed;

wherein the shield component is operatively attached to only said seat and the shield component further comprises a camera communicatively connected to a display screen, wherein the camera is configured to be positioned approximately at the individual's head region; and wherein the display screen presents content captured by and magnified from the camera;

wherein said suctioning component comprises a hose extending from said shield component to a ventilation system existing within the aircraft.

2. The system of claim 1, further comprising a release mechanism for detaching the shield component from the seat; and wherein the shield component is between four feet and four feet, six inches in length and between two feet and two feet, six inches in width.

3. The system of claim 1, wherein said display screen is located within the shield component.

4. The system of claim 1, wherein said display screen comprises a liquid crystal display screen.

5. The system of claim 1, wherein the shield component comprises glass or plastic.

6. The system of claim 1, wherein the shield component, the chamber component, and the suctioning component, comprise a single integrated unit.

7. The system of claim 1, wherein the shield component comprises light emitting diodes exuding configured to exude ultraviolet light toward an interior of the individual's mouth to disinfect the aerosols that are expelled from the individual.

8. The system of claim 1, wherein the shield component comprises plastic and wherein said plastic is polymethyl methacrylate.

* * * * *